United States Patent
Han et al.

(10) Patent No.: US 12,312,637 B2
(45) Date of Patent: May 27, 2025

(54) METHOD FOR PERFORMING PCR REACTION USING COMPREHENSIVE PCR REACTION SYSTEM

(71) Applicant: SHENYI BIOTECH (HANGZHOU) CO., LTD., Zhejiang (CN)

(72) Inventors: Qiaoling Han, Zhejiang (CN); Qiang Xu, Zhejiang (CN); Xiangmin Cui, Zhejiang (CN)

(73) Assignee: SHENYI BIOTECH (HANGZHOU) CO., LTD., Zhejiang (CN)

( * ) Notice: Subject to any disclaimer, the term of this patent is extended or adjusted under 35 U.S.C. 154(b) by 834 days.

(21) Appl. No.: 17/551,153

(22) Filed: Dec. 14, 2021

(65) Prior Publication Data
US 2022/0106626 A1   Apr. 7, 2022

Related U.S. Application Data

(63) Continuation of application No. PCT/CN2020/097142, filed on Jun. 19, 2020.

(30) Foreign Application Priority Data

Jul. 1, 2019  (CN) .......................... 201910585250.9
Jul. 1, 2019  (CN) .......................... 201910591817.3
(Continued)

(51) Int. Cl.
C12Q 1/686   (2018.01)
B01L 3/00    (2006.01)
B01L 7/00    (2006.01)

(52) U.S. Cl.
CPC ........ *C12Q 1/686* (2013.01); *B01L 3/502715* (2013.01); *B01L 3/502738* (2013.01);
(Continued)

(58) Field of Classification Search
CPC ..... B01L 2200/0621; B01L 2200/0684; B01L 2200/0689; B01L 2200/16; B01L 2200/10;
(Continued)

(56) References Cited

U.S. PATENT DOCUMENTS 5,605,798 A    2/1997 Köster
5,674,742 A   10/1997 Northrup et al.
(Continued)

FOREIGN PATENT DOCUMENTS

CN   1934272 A   3/2007
CN   1973197 A   5/2007
(Continued)

OTHER PUBLICATIONS

Espacenet English Translation of CN109661273 (Year: 2019).*
(Continued)

*Primary Examiner* — Kathryn Elizabeth Limbaugh

(57) ABSTRACT

Provided are a method for performing a PCR reaction using a PCR reaction system, a PCR reaction system, as well as a composition, a freeze-dried powder, and a diluent. The PCR reaction method includes: subjecting the piston to the first and second movement processings, to subject the diluent entering the injection chamber, the pyrolysis freeze-dried powder, and the sample to a first mixing processing; subjecting the first mixture to a pyrolysis processing; subjecting the piston to the third and fourth movement processings, to subject the pyrolysis liquid entering the injection chamber and the remaining diluent to a second mixing processing; subjecting the piston to the fifth and sixth movement processings, to allow the second mixture to enter the injection chamber and undergone a third mixing processing with the
(Continued)

freeze-dried powder of the reverse transcriptase and the PCR raw materials; and subjecting the third mixture to a PCR amplification processing.

20 Claims, 9 Drawing Sheets

(30) Foreign Application Priority Data

| | | | |
|---|---|---|---|
| Jul. 1, 2019 | (CN) | ......................... | 201910591847.4 |
| Jul. 1, 2019 | (CN) | ......................... | 201921011114.0 |
| Jul. 26, 2019 | (CN) | ......................... | 201910684842.6 |
| Oct. 9, 2019 | (CN) | ......................... | 201910953740.X |
| Oct. 9, 2019 | (CN) | ......................... | 201910953826.2 |
| Oct. 9, 2019 | (CN) | ......................... | 201910954105.3 |
| Oct. 9, 2019 | (CN) | ......................... | 201910954116.1 |
| Oct. 9, 2019 | (CN) | ......................... | 201921682904.1 |

(52) U.S. Cl.
CPC .......... *B01L 7/52* (2013.01); *B01L 2200/0689* (2013.01); *B01L 2200/16* (2013.01); *B01L 2300/044* (2013.01); *B01L 2300/0877* (2013.01); *B01L 2400/0478* (2013.01); *B01L 2400/0622* (2013.01); *C12Q 2527/125* (2013.01); *C12Q 2565/629* (2013.01)

(58) Field of Classification Search
CPC ....... B01L 2300/044; B01L 2300/0672; B01L 2300/0861; B01L 2300/0877; B01L 2400/0478; B01L 2400/0622; B01L 2400/0633; B01L 3/502715; B01L 3/502738; B01L 3/502761; B01L 3/5027; B01L 3/502753; B01L 7/52; C12Q 1/686; C12Q 1/6806; C12Q 2527/125; C12Q 2527/127; C12Q 2565/629; C12Q 2521/101; C12Q 2521/107; C12Q 2563/107

See application file for complete search history.

(56) References Cited

U.S. PATENT DOCUMENTS

| | | | |
|---|---|---|---|
| 2002/0068357 A1 | 6/2002 | Mathies et al. | |
| 2003/0162304 A1 | 8/2003 | Dority et al. | |
| 2007/0048194 A1 | 3/2007 | Schulein et al. | |
| 2010/0256350 A1 | 10/2010 | Rhee et al. | |
| 2011/0236960 A1 | 9/2011 | Bird et al. | |
| 2016/0243547 A1 | 8/2016 | Bar-Ziv et al. | |
| 2018/0010167 A1 | 1/2018 | Poritz et al. | |

FOREIGN PATENT DOCUMENTS

| | | | | |
|---|---|---|---|---|
| CN | 101613697 A | 12/2009 | | |
| CN | 101738379 A | 6/2010 | | |
| CN | 103221529 A | 7/2013 | | |
| CN | 103305499 A | 9/2013 | | |
| CN | 103642903 A | 3/2014 | | |
| CN | 103725600 A | 4/2014 | | |
| CN | 103911367 A | 7/2014 | | |
| CN | 103946364 A | 7/2014 | | |
| CN | 103988082 A | 8/2014 | | |
| CN | 104673625 A | 6/2015 | | |
| CN | 104846121 A | 8/2015 | | |
| CN | 104955948 A | 9/2015 | | |
| CN | 105026931 A | 11/2015 | | |
| CN | 105349401 A | 2/2016 | | |
| CN | 105463125 A | 4/2016 | | |
| CN | 104673625 B | 2/2017 | | |
| CN | 106701566 A | 5/2017 | | |
| CN | 206375900 U | 8/2017 | | |
| CN | 107460121 A | 12/2017 | | |
| CN | 107904156 A | 4/2018 | | |
| CN | 207210392 U | 4/2018 | | |
| CN | 108004129 A | 5/2018 | | |
| CN | 108342383 A | 7/2018 | | |
| CN | 108546736 A | 9/2018 | | |
| CN | 108642148 A | 10/2018 | | |
| CN | 207933420 U | 10/2018 | | |
| CN | 108913530 A | 11/2018 | | |
| CN | 108998506 A | 12/2018 | | |
| CN | 109022386 A | 12/2018 | | |
| CN | 208414422 U | 1/2019 | | |
| CN | 109306350 A | 2/2019 | | |
| CN | 109371008 A | 2/2019 | | |
| CN | 109488787 A | 3/2019 | | |
| CN | 109609627 A | 4/2019 | | |
| CN | 109661273 A | * | 4/2019 | ........ B01L 3/502715 |
| CN | 109790506 A | 5/2019 | | |
| CN | 208964948 U | 6/2019 | | |
| CN | 211339446 U | 8/2020 | | |
| EP | 1143252 A4 | 1/2007 | | |
| EP | 2875866 A1 | 5/2015 | | |
| JP | 2017516083 A | 6/2017 | | |
| MX | 2009013417 A | 6/2011 | | |
| WO | 2018140966 A1 | 8/2018 | | |

OTHER PUBLICATIONS

Hong Yu, Fangfang Peng, Fang Liu, "Chapter 11 Biochip", Experimental Techniques in Medical Biochemistry and Molecular Biology, Sep. 30, 2003, pp. 290-296, published by National Excellent Publishing House, Wuhan University Press.

Lei Luo, Wei Hou, Jun Yu, "Novel Real-Time Fluorescent PCR Chip Applied to Examine the Ankylosing Spondylitis", Analytical Letters, 43: 12-21, 2010, DOI: 10.1080/00032710802677167.

Qiangyuan Zhu, "Self-priming Compartmentalization Digital PCR Chip for Single Nucleic Acid and Protein Molecule Detection", Chinese Doctoral Dissertations Full-text Database (Master) Medicine and Health Sciences, Issue 08, 2013, pp. 1-174.

The extended European search report in European Patent Application No. 20834221.2, dated Sep. 2, 2022.

Rejection Decision in counterpart China Application No. 201910953826. 2, dated Sep. 19, 2022.

The Notification to Grant Patent Right for Invention in counterpart Chinese Application No. 201910954116.1, dated Feb. 23, 2022.

First Office Action dated Aug. 30, 2024 received in corresponding patent family application No. CN201910953740.X. English translation attached.

Wang, Jiangling et al., "Method of extract DNA from a single nematode", Plant Quarantine, vol. 25, No. 2, pp. 32-35, Mar. 15, 2011.

Michella Hanna et al., "Isolation of Nucleic Acids", Methods in Molecular Biology, vol. 313: Yeast Protocol: Second Edition, Dec. 31, 2006, pp. 15-20.

Zhi-Yong Hou et al., "A new buffer for allele-specific PCR of human whole blood and filter paper-dried blood", Chinese Journal of New Drugs, 2016, vol. 25, No. 24, pp. 2876-2880.

Betty A. Forbes et al., "Substances Interfering with Direct Detection of *Mycobacterium tuberculosis* in Clinical Specimens by PCR: Effects of Bovine Serum Albumin", Journal of Clinical Microbiology, Sep. 1996, vol. 34, No. 9, pp. 2125-2128.

The First Office Action in counterpart Chinese Application No. 201910953826.2, dated Nov. 29, 2021.

The First Office Action in counterpart Chinese Application No. 201910954105.3, dated Dec. 1, 2021.

The Second Office Action in counterpart China Application No. 201910954105.3, dated Jun. 6, 2022.

Notice of Decision of Granting Patent Right for Invention in counterpart China Application No. 201910954105.3, dated Jul. 27, 2022.

The Second Office Action in counterpart China Application No. 201910953826.2, dated May 26, 2022.

(56) References Cited

OTHER PUBLICATIONS

Chen, Shengming, Economic microbiology, Sep. 30, 1997, p. 118, Chengdu University of Science and Technology Press, Chengdu, China.
Chen, Shangcai et al., Clinicopathological histology and immunohistochemical diagnostics, May 31, 1999, p. 33, Shanghai Medical University Press, Shanghai, China.
Zhou, Qin, Medical molecular biology experiment tutorial, Mar. 31, 2008, p. 79, Sun Yat-sen University Press, Guangzhou, China.
Wang, Dongfeng et al., Food Quality and safety Testing technology, the 3rd edition, Jul. 31, 2018, pp. 251-252, China Light Industry Press, Beijing, China.

* cited by examiner

METHOD FOR PERFORMING PCR REACTION USING COMPREHENSIVE PCR REACTION SYSTEM

CROSS-REFERENCE TO RELATED APPLICATIONS

The present application is a continuation of International Patent Application No. PCT/CN2020/097142, filed on Jun. 19, 2020, which claims priority to Chinese patent application NO. 201910585250.9, filed on Jul. 1, 2019; Chinese patent application NO. 201921011114.0, filed on Jul. 1, 2019; Chinese patent application NO. 201910591847.4, filed on Jul. 1, 2019; Chinese patent application NO. 201910591817.3, filed on Jul. 1, 2019; Chinese patent application NO. 201910684842.6, filed on Jul. 26, 2019; Chinese patent application NO. 201910954116.1, filed on Oct. 9, 2019; Chinese patent application NO. 201921682904.1, filed on Oct. 9, 2019; Chinese patent application NO. 201910953740.X, filed on Oct. 9, 2019; Chinese patent application NO. 201910953826.2, filed on Oct. 9, 2019; and Chinese patent application NO. 201910954105.3, filed on Oct. 9, 2019, the entire contents of which are incorporated herein by their references.

FIELD

The present disclosure relates to the field of molecular biology. Specifically, the present disclosure relates to a method for performing a PCR reaction using a PCR reaction system.

BACKGROUND

The conventional PCR reaction process is generally carried out separately. That is, the required nucleic acid is first extracted with a nucleic acid extraction kit, then the extracted nucleic acid and reagents are mixed and added into a PCR reaction tube, and finally the PCR reaction tube is placed into a PCR instrument for the PCR amplification reaction, so as to obtain the final result. The conventional PCR reaction process has complicated operation steps and low work efficiency.

Therefore, there is a need to further study and develop a simple and efficient PCR reaction process.

SUMMARY

The present disclosure is based on Applicant's discovery and understanding of the following facts and problems.

The conventional PCR reaction process has complicated operation steps and low work efficiency. Investigating the reasons thereof, Applicant found that each step in the conventional PCR reaction process generally requires operations of professionals, and these operations generally need to be performed separately by different instruments, such as nucleic acid purifiers and fully automated workstations. In addition, the operations of the whole process are also required to be carried out in a standard PCR laboratory environment. In view of the above problems, Applicant integrated the extraction of nucleic acid, the mixing of nucleic acid and reagents, and the final PCR reaction into one system through microfluidic pipelines. The method for performing PCR reactions with this system can truly realize complete automation, and solve the problem that the conventional PCR experiment process needs to be operated by professionals in a professional experimental environment, thereby reducing the manual errors, significantly improving the working efficiency of the PCR reaction, and greatly saving the cost of human resources.

To this end, in one aspect of the present disclosure, the present disclosure provides a method for performing a PCR reaction using a PCR reaction system. According to an embodiment of the present disclosure, the PCR reaction system includes a sample containing unit having a pyrolysis freeze-dried powder and a sample provided therein the sample containing unit including a first liquid outlet/inlet; a diluent containing unit having a diluent provided therein, the diluent containing unit including a diluent outlet; a PCR reaction unit having a freeze-dried powder of a reverse transcriptase and PCR raw materials provided therein, the PCR reaction unit including a PCR reaction solution outlet and a pyrolyzed sample mixture inlet; and a piston unit including an injection chamber and a piston, the injection chamber including a second liquid outlet/inlet. The second liquid outlet/inlet is connected to the first liquid outlet/inlet through a first pipeline, the second liquid outlet/inlet is connected to the diluent outlet through a second pipeline, the second liquid outlet/inlet is connected to the pyrolyzed sample mixture inlet through a third pipeline, and the PCR reaction solution outlet is connected to the diluent outlet through a fourth pipeline. The method includes: subjecting the piston to a first movement processing, to allow a part of the diluent to enter the injection chamber, where the diluent is provided in the diluent containing unit; subjecting the piston to a second movement processing, to subject the part of the diluent entering the injection chamber, the pyrolysis freeze-dried powder, and the sample to a first mixing processing, where the pyrolysis freeze-dried powder and the sample are provided in the sample containing unit, the first mixing processing is performed in the sample containing unit; subjecting a product of the first mixing processing to a pyrolysis processing, where the pyrolysis processing is performed in the sample containing unit; subjecting the piston to a third movement processing, to allow a product of the pyrolysis processing to enter the injection chamber; subjecting the piston to a fourth movement processing, to subject the product of the pyrolysis processing entering the injection chamber and the remaining part of the diluent to a second mixing processing, where the second mixing process is performed in the diluent containing unit; subjecting the piston to a fifth movement processing, to allow a product of the second mixing processing to enter the injection chamber; subjecting the piston to a sixth movement processing, to subject the product of the second mixing processing entering the injection chamber, the freeze-dried powder of the reverse transcriptase and the PCR raw materials to a third mixing processing, where the freeze-dried powder of the reverse transcriptase and the PCR raw materials are provided in the PCR reaction unit, and the third mixing processing is performed in the PCR reaction unit; and subjecting a product of the third mixing processing to a PCR temperature cycle amplification processing, where the PCR temperature cycle amplification process is performed in the PCR reaction unit.

In the PCR reaction system according to embodiments of the present disclosure, the sample containing unit, the diluent containing unit, the PCR reaction unit, and the piston unit are connected to each other through microfluidic pipelines; and respective units are independently provided units, such that the respective units store different reactants before use, which is conducive to long-term storage of reactants when not in use. For example, the independent setting of the sample containing unit is conducive to separately adding samples, thereby simplifying the operation of adding samples, and also facilitating the long-term storage of samples. First, the piston is pulled outward to a certain position, to allow a part of the diluent in the diluent containing unit to flow to the injection chamber; then the piston is moved back and forth to allow the diluent in the injection chamber to enter the sample containing unit, and to be mixed evenly with the pyrolysis freeze-dried powder and the sample in the sample containing unit at the same time; then the sample containing unit is heated to a set temperature, so that the sample in the sample containing unit is fully pyrolyzed at the set temperature; after the pyrolysis is completed, the piston is pulled outward again to a certain position, allowing the pyrolyzed sample mixture in the sample containing unit to flow to the injection chamber; then the piston is moved back and forth, such that the pyrolyzed sample mixture in the injection chamber returns to the diluent containing unit and is mixed evenly with the remaining diluent in the diluent containing unit at the same time, thereby diluting the pyrolyzed sample mixture and reducing a concentration of impurities therein; afterwards, the piston is pulled outward again to a certain position, to allow the diluted sample mixture in the diluent containing unit to flow to the injection chamber; then the piston is moved back and forth, such that the diluted sample mixture in the injection chamber enters the PCR reaction unit and is mixed evenly with the freeze-dried powder of the reverse transcriptase and the PCR raw materials in the PCR reaction unit at the same time; and finally, the PCR reaction unit is subjected to a PCR temperature increasing control, so as to complete the PCR amplification reaction. The method according to the embodiment of the present disclosure truly realizes complete automation, and solves the problem that the conventional PCR experiment process needs to be operated by professionals in a professional experimental environment, thereby reducing the manual errors, significantly improving the working efficiency of the PCR reaction, and greatly saving the cost of human resources.

According to an embodiment of the present disclosure, the above-mentioned method may further include at least one of the following additional technical features.

According to an embodiment of the present disclosure, the PCR temperature cycle amplification processing includes: subjecting the product of the third mixing processing to a constant temperature processing; and subjecting a product of the constant temperature processing to a temperature cycle processing.

According to an embodiments of the present disclosure, the PCR reaction system further includes: a sample control valve provided on the first pipeline and configured to control a connection state between the first liquid outlet/inlet and the second liquid outlet/inlet; a dilution control valve provided on the second pipeline and configured to control a connection state between the diluent outlet and the second liquid outlet/inlet; a first PCR control valve provided on the third pipeline and configured to control a connection state between the pyrolyzed sample mixture inlet and the second liquid outlet/inlet; and a second PCR control valve provided on the fourth pipeline and configured to control a connection state between the diluent outlet and the PCR reaction solution outlet. The method further includes: prior to the first movement processing, closing the sample control valve, the first PCR control valve, and the second PCR control valve, and opening the dilution control valve; subsequent to the first movement processing and prior to the second movement processing, closing the dilution control valve and opening the sample control valve; subsequent to the third movement processing and prior to the fourth movement processing, closing the sample control valve and opening the dilution control valve; subsequent to the fifth movement processing and prior to the sixth movement processing, closing the dilution control valve, and opening the first PCR control valve and the second PCR control valve; and subsequent to the constant temperature processing and prior to the temperature cycle processing, closing the first PCR control valve and the second PCR control valve. In this way, the method according to the embodiment of the present disclosure is carried out in a sealed environment, which reduces the pollution to the system environment and improves the credibility of the experiment, and the operation is more convenient.

According to an embodiment of the present disclosure, the PCR reaction system further includes a buffering unit provided on the fourth pipeline and including a PCR reaction solution inlet and a vent, the second PCR control valve is connected to the PCR reaction solution inlet, and the diluent outlet is connected to the vent. In this way, the method according to the embodiment of the present disclosure can solve the problem of overflowing of PCR reagents when expanding at high temperature, and the method is performed in a sealed environment, which reduces the pollution to the system environment and improves the credibility of the experiment, and the operation is more convenient.

According to an embodiment of the present disclosure, the PCR reaction system further includes: a sample containing unit seal provided on a surface of the first liquid outlet/inlet and configured to be used in a first sealing processing of the sample containing unit; and a diluent containing unit seal provided on a surface of the diluent outlet and configured to be used in a second sealing processing of the diluent containing unit. The method further includes: a pre-piercing processing. The pre-piercing processing includes subjecting the sample containing unit seal to a first piercing processing in advance, and subjecting the diluent containing unit seal to a second piercing processing in advance. Applicant found that the sample containing unit seal and the diluent containing unit seal can not only isolate the reactants in the respective independent units, being conducive to the long-term storage of the reactants when not in use, greatly prolonging the storage time of each reactant in each unit, but also protect the PCR reaction system from being polluted by the reactants, and prolong the service life of the PCR reaction system. In this way, when the sample containing unit is added with a sample, it is only required to pierce the sample containing unit seal and the diluent containing unit seal to allow the sample containing unit and the diluent containing unit to be in a connection state with the microfluidic pipelines, and thus the system can start working. Therefore, the operation of the method according to the embodiment of the present disclosure is more convenient.

According to an embodiment of the present disclosure, the first piercing processing is performed by a piercing device for the sample containing unit seal, and the second piercing processing is performed by a piercing device for the diluent containing unit seal.

According to an embodiment of the present disclosure, at least one of the diluent containing unit seal and the sample containing unit seal is a sealing film.

According to an embodiment of the present disclosure, the sealing film is formed of at least one of a tin foil paper, a laminating film, or a kraft paper.

According to an embodiment of the present disclosure, the sealing film has a thickness ranging from 0.01 mm to 0.2 mm, for example, 0.03 mm, 0.05 mm, 0.07 mm, 0.09 mm, 0.1 mm, 0.13 mm, 0.15 mm, 0.17 mm, or 0.19 mm. Applicant found that if the sealing film is too thin, it may be permeable, but if the sealing film is too thick, it will be difficult to be pierced. In some embodiments, the thickness of the sealing film ranges from 0.05 mm to 0.1 mm.

In another aspect of the present disclosure, the present disclosure provides a PCR reaction system. According to an embodiment of the present disclosure, the system includes: a sample containing unit having a freeze-dried powder of pyrolysis raw materials provided therein, the sample containing unit including a first liquid outlet/inlet; a diluent containing unit having a diluent provided therein, the diluent containing unit including a diluent outlet; a PCR reaction unit having a freeze-dried powder of a reverse transcriptase and PCR raw materials provided therein, the PCR reaction unit including a PCR reaction solution outlet and a pyrolyzed sample mixture inlet; and a piston unit including an injection chamber and a piston, the injection chamber including a second liquid outlet/inlet. The second liquid outlet/inlet is connected to the first liquid outlet/inlet through a first pipeline, the second liquid outlet/inlet is connected to the diluent outlet through a second pipeline, the second liquid outlet/inlet is connected to the pyrolyzed sample mixture inlet through a third pipeline, and the PCR reaction solution outlet is connected to the diluent outlet through a fourth pipeline.

In the PCR reaction system according to the embodiment of the present disclosure, the sample containing unit, the diluent containing unit, the PCR reaction unit, and the piston unit are connected to each other through microfluidic pipelines; and each unit is an independent unit, such that respective units store different reactants before use, which is conducive to long-term storage of reactants when not in use. For example, the independent setting of the sample containing unit is conducive to separately adding samples, thereby simplifying the operation of adding samples, and also facilitating the long-term storage of samples. First, the piston is pulled outward to a certain position to allow a part of the diluent in the diluent containing unit to flow to the injection chamber; then the piston is moved back and forth to allow the diluent in the injection chamber to enter the sample containing unit, and to be mixed evenly with the freeze-dried powder of pyrolysis materials and the sample in the sample containing unit at the same time; then the sample containing unit is heated to a set temperature, so that the sample in the sample containing unit is fully pyrolyzed at the set temperature; after the pyrolysis is completed, the piston is pulled outward again to a certain position, allowing the pyrolyzed sample mixture in the sample containing unit to flow to the injection chamber; then the piston is moved back and forth, such that the pyrolyzed sample mixture in the injection chamber returns to the diluent containing unit and is mixed evenly with the remaining diluent in the diluent containing unit at the same time, thereby diluting the pyrolyzed sample mixture and reducing a concentration of impurities therein; afterwards, the piston is pulled outward again to a certain position, to allow the diluted sample mixture in the diluent containing unit to flow to the injection chamber; then the piston is moved back and forth, such that the diluted sample mixture in the injection chamber enters the PCR reaction unit and is mixed evenly with the reverse transcriptase and the freeze-dried powder of PCR raw materials in the PCR reaction unit at the same time; and finally, the PCR reaction unit is subjected to a PCR temperature increasing control, so as to complete the PCR amplification reaction. The PCR reaction system according to the embodiment of the present disclosure truly realizes a fully automated operation, and solves the problem that the conventional PCR experiment process needs to be operated by professionals in a professional experimental environment, thereby reducing the manual errors, significantly improving the working efficiency of the PCR reaction, and greatly saving the cost of human resources.

According to embodiments of the present disclosure, the above-mentioned system may further include at least one of the following additional technical features.

According to an embodiment of the present disclosure, the system further includes: a sample control valve provided on the first pipeline and configured to control a connection state between the first liquid outlet/inlet and the second liquid outlet/inlet; a dilution control valve provided on the second pipeline and configured to control a connection state between the diluent outlet and the second liquid outlet/inlet; a first PCR control valve provided on the third pipeline and configured to control a connection state between the pyrolyzed sample mixture inlet and the second liquid outlet/inlet; and a second PCR control valve provided on the fourth pipeline and configured to control a connection state between the diluent outlet and the PCR reaction solution outlet. In this way, the PCR reaction performed by using the PCR reaction system according to the embodiment of the present disclosure is carried out in a sealed environment, which reduces the pollution to the system environment and improves the credibility of the experiment, and the operation is more convenient.

According to an embodiment of the present disclosure, the system further includes a buffering unit provided on the fourth pipeline and comprising a PCR reaction solution inlet and a vent, the second PCR control valve is connected to the PCR reaction solution inlet, and the diluent outlet is connected to the vent. In this way, the PCR reaction system according to the embodiment of the present disclosure can solve the problem of overflowing of PCR reagents when expanding at high temperature.

According to an embodiment of the present disclosure, the system further includes: a sample containing unit seal provided on a surface of the first liquid outlet/inlet and configured to be used in a first sealing processing of the sample containing unit; and a diluent containing unit seal provided on a surface of the diluent outlet and configured to be used in a second sealing processing of the diluent containing unit. Applicant found that the sample containing unit seal and the diluent containing unit seal can not only isolate the reactants in the respective independent units, being conducive to the long-term storage of the reactants when not in use, greatly prolonging the storage time of each reactant in each unit, but also protect the PCR reaction system from being polluted by the reactants, and prolong the service life of the PCR reaction system.

According to an embodiment of the present disclosure, the system further includes: a piercing device for the sample containing unit seal, for use in a first piercing processing of the sample containing unit seal, and a piercing device for the diluent containing unit seal, for use in a second piercing processing of the diluent containing unit seal.

According to an embodiment of the present disclosure, at least one of the diluent containing unit seal and the sample containing unit seal is a sealing film.

According to an embodiment of the present disclosure, the sealing film is formed of at least one of a tin foil paper, a laminating film, or a kraft paper.

According to an embodiment of the present disclosure, the sealing film has a thickness ranging from 0.01 mm to 0.2 mm, for example, 0.03 mm, 0.05 mm, 0.07 mm, 0.09 mm, 0.1 mm, 0.13 mm, 0.15 mm, 0.17 mm, or 0.19 mm. Applicant found that if the sealing film is too thin, it may be permeable, but if the sealing film is too thick, it will be difficult to be pierced. In some embodiments, the thickness of the sealing film ranges from 0.05 mm to 0.1 mm.

According to an embodiment of the present disclosure, the freeze-dried powder of pyrolysis raw materials includes a metal ion chelating agent, sodium dodecyl sulfate, saponin, proteinase K, polyethylene glycol 3350, Tris-HCl, and water; and the freeze-dried powder of the reverse transcriptase and the PCR raw materials comprises mannitol, sucrose, chloride salt, bovine serum albumin, dNTP, polyoxyethylene lauryl ether, HEPES, DNA polymerase, reverse transcriptase and RNase inhibitor, and water. In some embodiments, the metal ion chelating agent is EDTA and EGTA. In some embodiments, the chloride salt is potassium chloride and magnesium chloride.

According to an embodiment of the present disclosure, the diluent comprises polyol, chloride salt, Tris-HCl, surfactant, and water. In some embodiments, the polyol is glycerol.

In addition, Applicant found that, on the one hand, the reagents, such as phenol, chloroform, guanidine hydrochloride, ethanol, guanidine isothiocyanate, etc., used during sample extraction are not only harmful to humans, but may even cause cancer in serious cases; and some reagents are flammable, which has higher requirements on the laboratory environment and safety risk control; moreover, these reagents are also easy to cause air and water pollution. On the other hand, the preparation and dispensing of fluorescent quantitative PCR reagents must be carried out in the standard reagent preparation room to prevent sample contamination, and the preparation and dispensing operations are complicated and require specially trained personnel. Based on the above problems, Applicant has conducted research and developed a composition, including a first component that can be used effectively for sample pyrolysis and nucleic acid extraction, and a second component that can be used effectively for PCR amplification reaction. Compared with the existing reagents, the first component has significantly reduced toxicity and pollution, and significantly improved safety and stability, which is advantageous for transportation and storage and has lower requirements for samples. Compared with the related art, the second component has significantly improved stability, which is beneficial to transportation and storage, and lowers the requirements for the experimental environment. Through combined use of the first component and the second component, the lysis of the sample, the extraction of nucleic acid, and the preparation of fluorescent quantitative PCR reagents can be completed in absence of professionals, thereby reducing the technical requirements for operators, while providing excellent PCR amplification effect.

For this reason, in another aspect of the present disclosure, the present disclosure provides a composition for PCR reaction. According to an embodiment of the present disclosure, the composition includes a first component and/or a second component. The first component includes a metal ion chelating agent, sodium dodecyl sulfate (SDS), saponin, proteinase K, polyethylene glycol 3350 (PEG 3350), Tris-HCl, and water. The second component includes mannitol, sucrose, chloride salt, bovine serum albumin (BSA), dNTPs, polyoxyethylene lauryl ether (Brij 35), HEPES, DNA polymerase, reverse transcriptase and RNase inhibitor, and water. In some embodiments, the metal ion chelating agent is EDTA and EGTA. In some embodiments, the chloride salt is potassium chloride and magnesium chloride. The first component in the composition according to the embodiment of the present disclosure can be effectively used for sample pyrolysis and nucleic acid extraction in combination with the heating function of other instruments, and the second component can be effectively used for PCR amplification reaction. Applicant found that, compared with the existing reagents, the first component has significantly reduced toxicity and pollution, and significantly improved safety, such that the mixture obtained after the sample is pyrolyzed by the first component no longer needs to be purified separately, and can be used directly used in the subsequent PCR reaction, thereby lowering the requirements on the sample; compared with the related art, the second component is stable and effective, which is advantageous for transportation and storage, thereby lowering the requirements for transportation and storage temperature. Through the combined use of the first and second components, the lysis of the sample, the extraction of nucleic acid, and the preparation of fluorescent quantitative PCR reagents can be completed in absence of professionals, thereby reducing the technical requirements for operators, while providing excellent PCR amplification effect.

According to an embodiment of the present disclosure, the above-mentioned composition may further include at least one of the following additional technical features.

According to an embodiment of the present disclosure, based on a total volume of the first component, a concentration of the EDTA ranges from 0.1 mmol/L to 10 mmol/L, for example, 0.5 mmol/L, 0.7 mmol/L, 1.0 mmol/L, 2.0 mmol/L, 3.0 mmol/L, or 4.0 mmol/L; a concentration of the EGTA ranges from 0.1 mmol/L to 15 mmol/L, for example, 0.5 mmol/L, 0.7 mmol/L, 3 mmol/L, 5 mmol/L, 7 mmol/L, 10 mmol/L, or 13 mmol/L; a concentration of the proteinase K ranges from 5 U/mL to 150 U/mL, for example, 7 U/mL, 10 U/mL, 15 U/mL, 30 U/mL, 45 U/mL, 60 U/mL, 75 U/mL, 90 U/mL, or 120 U/mL; a concentration of the sodium dodecyl sulfate ranges from 0.1% to 3.0%, for example, 0.3%, 0.5%, 1.0%, 1.5%, 2.0%, or 2.5%; a concentration of the saponin ranges from 0.1% to 3.0%, for example, 0.3%, 0.5%, 1.0%, 1.5%, 2.0%, or 2.5%; and a concentration of the polyethylene glycol 3350 ranges from 0.1% to 5.0%, for example, 0.3%, 0.5%, 1.0%, 1.5%, 2.0%, 2.5%, 3.0%, 3.5%, 4.0%, or 4.5%. It should be noted that the concentrations of the sodium dodecyl sulfate, the saponin and the polyethylene glycol 3350 are mass volume concentrations, i.e., the mass of sodium dodecyl sulfate, saponin or polyethylene glycol 3350 per 100 mL of solution, in unit of gram. For example, that the concentration of the sodium dodecyl sulfate ranges 0.1% to 3.0% indicates that the mass of sodium dodecyl sulfate per 100 mL of the first component ranges from 0.1 g to 3.0 g. Applicant found that, when the concentrations of respective ingredients in the first component are within the above ranges, the first component can be further effectively used for sample pyrolysis and nucleic acid extraction, with further reduced toxicity and pollution, and higher safety, thereby lowering the requirements on the sample, and further improving subsequent PCR amplification effect.

According to an embodiment of the present disclosure, based on the total volume of the first component, the concentration of the EDTA ranges from 0.5 mmol/L to 5 mmol/L; the concentration of the EGTA ranges from 0.5 mmol/L to 10 mmol/L; the concentration of the proteinase K ranges from 10 U/mL to 100 U/mL; the concentration of the sodium dodecyl sulfate ranges from 0.5% to 2.5%; the concentration of the saponin ranges from 0.5% to 2.5%; and the concentration of the polyethylene glycol 3350 ranges from 0.5% to 4.5%. Applicant found that, when the concentrations of the respective ingredients in the first component are within the above ranges, the first component can be further effectively used for sample pyrolysis and nucleic acid extraction, with further reduced toxicity and pollution, and higher safety, thereby lowering the requirements on the sample, and further improving subsequent PCR amplification effect.

According to an embodiment of the present disclosure, the Tris-HCl is provided in a form dissolved in water. It should be noted that the Tris-HCl is a type of buffer material commonly used in this field, which can be instantly prepared or directly purchased.

According to embodiments of the present disclosure, the pH of a solution formed by dissolving Tris-HCl in water ranges from 7.5 to 8.2, such as 7.6, 7.7, 7.8, 7.9, 8.0, or 8.1. It should be noted that said pH does not refer to the pH of the first component, but the pH of the solution formed by dissolving Tris-HCl in water. According to an embodiment of the present disclosure, when the pH of the solution formed by dissolving Tris-HCl in water ranges from 7.5 to 8.2, Tris-HCl has a better buffering effect on the first component, which is more conducive to the sample pyrolysis and the nucleic acid extraction, with higher stability, thereby further improving the subsequent PCR amplification effect. In some embodiments, the pH of the solution formed by dissolving Tris-HCl in water is 7.6.

According to an embodiment of the present disclosure, based on the total volume of the first component, the concentration of the Tris-HCl ranges from 1 mmol/L to 25 mmol/L, for example, 2 mmol/L, 4 mmol/L, 5 mmol/L, 6 mmol/L, 8 mmol/L, 10 mmol/L, 12 mmol/L, 14 mmol/L, 16 mmol/L, 18 mmol/L, 20 mmol/L, 22 mmol/L, or 24 mmol/L. According to an embodiment of the present disclosure, when the concentration of the Tris-HCl ranges from 1 mmol/L to 25 mmol/L, the Tris-HCl has a better buffering effect on the first component, which is more conducive to the sample pyrolysis and the nucleic acid extraction, with higher stability, thereby further improving the subsequent PCR amplification effect. In some embodiments, the concentration of the Tris-HCl ranges from 5 mmol/L to 20 mmol/L.

According to an embodiment of the present disclosure, based on a total volume of the second component, a concentration of the potassium chloride ranges from 10 mmol/L to 150 mmol/L, for example, 15 mmol/L, 20 mmol/L, 30 mmol/L, 40 mmol/L, 60 mmol/L, 80 mmol/L, 100 mmol/L, or 120 mmol/L; a concentration of the magnesium chloride ranges from 0.5 mmol/L to 10.0 mmol/L, for example, 0.7 mmol/L, 1.0 mmol/L, 2.0 mmol/L, 3.0 mmol/L, 4.0 mmol/L, 5.0 mmol/L, 7.0 mmol/L, or 10.0 mmol/L; a concentration of the dNTPs ranges from 150 µmol/L to 250 µmol/L, for example, 180 µmol/L, 200 µmol/L, or 230 µmol/L; a concentration of the DNA polymerase ranges from 10 U/mL to 250 U/mL, for example, 13 U/mL, 15 U/mL, 18 U/mL, 20 U/mL, 30 U/mL, 50 U/mL, 80 U/mL, 100 U/mL, 120 U/mL, 150 U/mL, 180 U/mL, 200 U/mL, or 230 U/mL; a concentration of the reverse transcriptase ranges from 5 U/mL to 100 U/mL, for example, 7 U/mL, 10 U/mL, 20 U/mL, 30 U/mL, 40 U/mL, 50 U/mL, 70 U/mL, or 90 U/mL; a concentration of the RNase inhibitor ranges from 100 U/mL to 1000 U/mL, for example, 150 U/mL, 200 U/mL, 300 U/mL, 500 U/mL, 700 U/mL, or 900 U/mL; a concentration of the mannitol ranges from 0.1% to 10%, for example, 0.2%, 0.4%, 0.5%, 1.0%, 3.0%, 5.0%, 7.0%, or 9.0%; a concentration of the sucrose ranges from 0.1% to 10%, for example, 0.2%, 0.4%, 0.5%, 1.0%, 3.0%, 5.0%, 7.0%, or 9.0%; a concentration of the bovine serum albumin ranges from 0.1 mg/mL to 5 mg/mL, for example, 0.2 mg/mL, 0.4 mg/mL, 0.6 mg/mL, 0.8 mg/mL, 1.0 mg/mL, 2.0 mg/mL, 3.0 mg/mL, or 4.0 mg/mL; and a concentration of the polyoxyethylene lauryl ether ranges from 0.01% to 0.10%, for example, 0.02%, 0.03%, 0.04%, 0.05%, 0.06%, 0.07%, 0.08%, or 0.09%. It should be noted that the concentrations of the sucrose and the polyoxyethylene lauryl ether are mass volume concentrations, i.e., the mass of the sucrose or polyoxyethylene lauryl ether per 100 mL of solution, in unit of gram. For example, that the concentration of the sucrose ranges from 0.1% to 10% indicates that the mass of sucrose per 100 mL of the second component ranges from 0.1 g to 10 g. That the concentration of the mannitol ranges 0.1% to 10% indicates a volume of the mannitol per 100 mL of the second component ranges from 0.1 mL to 10 mL. Applicant found that, when the concentrations of respective ingredients in the second component are within these ranges, the second component can be further effectively used in the PCR amplification reaction, the PCR amplification effect is better, while the stability is higher.

According to an embodiment of the present disclosure, based on the total volume of the second component, the concentration of the potassium chloride ranges from 20 mmol/L to 100 mmol/L; the concentration of the magnesium chloride ranges from 1.0 mmol/L to 5.0 mmol/L; the concentration of the dNTPs is 200 µmol/L; the concentration of the DNA polymerase ranges from 20 U/mL to 200 U/mL; the concentration of the reverse transcriptase ranges from 10 U/mL to 50 U/mL; the concentration of the RNase inhibitor ranges from 200 to 1000 U/mL; the concentration of the mannitol ranges from 0.5% to 8%; the concentration of the sucrose ranges from 0.5% to 8%; the concentration of the bovine serum albumin ranges from 0.1 mg/mL to 1 mg/mL; and the concentration of the polyoxyethylene lauryl ether is 0.05%. Applicant found that, when the concentrations of respective constituents in the second component are within these ranges, the second component can be further effectively used in the PCR amplification reaction, the PCR amplification effect is better, while the stability is higher.

According to an embodiment of the present disclosure, the HEPES is provided in a form dissolved in water. It should be noted that the HEPES is a type of buffer material commonly used in this field, which can be instantly prepared or directly purchased.

According to an embodiment of the present disclosure, the pH of a solution formed by dissolving HEPES in water ranges from 8.0 to 8.5, for example, 8.1, 8.2, 8.25, 8.3, or 8.4. It should be noted that said pH does not refer to the pH of the second component, but the pH of the solution formed by dissolving HEPES in water. According to an embodiment of the present disclosure, when the pH of the solution formed by dissolving HEPES in water ranges from 8.0 to 8.5, the HEPES has a better buffering effect on the second component, which is more conducive to the PCR amplification reaction, the PCR amplification effect is better, while the stability is higher. In some embodiments, the pH of the solution formed by dissolving HEPES in water is 8.25.

According to an embodiment of the present disclosure, based on the total volume of the second component, the concentration of the HEPES ranges from 5 mmol/L to 55 mmol/L, for example, 10 mmol/L, 15 mmol/L, 20 mmol/L, 25 mmol/L, 30 mmol/L, 35 mmol/L, 40 mmol/L, 45 mmol/L, or 50 mmol/L. According to an embodiment of the present disclosure, when the concentration of the HEPES ranges from 5 mmol/L to 55 mmol/L, the HEPES is more conducive to the PCR amplification reaction, the PCR amplification effect is better, while the stability is higher. In some embodiments, the concentration of the HEPES ranges from 10 mmol/L to 50 mmol/L.

According to an embodiment of the present disclosure, the saponin includes at least one selected from the group consisting of tea saponin, ginsenoside, polyphyllin, and soyasaponin.

According to an embodiment of the present disclosure, the DNA polymerase includes at least one selected from the group consisting of Taq enzyme and Tth DNA polymerase.

According to an embodiment of the present disclosure, the reverse transcriptase includes at least one selected from the group consisting of M-MLV reverse transcriptase, and AMV reverse transcriptase.

According to an embodiment of the present disclosure, the RNase inhibitor includes at least one selected from the group consisting of diethyl pyrophosphate, guanidine isothiocyanate, ribonucleoside vanadyl complex, RNasin, urea, and diatomite.

In another aspect of the present disclosure, the present disclosure provides a composition. According to an embodiment of the present disclosure, the composition includes a first component and/or a second component. Based on a total volume of the first component, the first component includes EDTA at a concentration of 0.5 mmol/L to 5 mmol/L, EGTA at a concentration of 0.5 mmol/L to 10 mmol/L, proteinase K at a concentration of 10 U/mL to 100 U/mL, sodium dodecyl sulfate at a concentration of 0.5% to 2.5%, saponin at a concentration of 0.5% to 2.5%, polyethylene glycol 3350 at a concentration of 0.5% to 4.5%, Tris-HCl at a concentration of 5% to 20 mmol/L, and water. Based on the total volume of the second component, the second component includes potassium chloride at a concentration of 20 mmol/L to 100 mmol/L, magnesium chloride at a concentration of 1.0 mmol/L to 5.0 mmol/L, dNTPs at a concentration of 200 µmol/L, DNA polymerase at a concentration of 20 U/mL to 200 U/mL, reverse transcriptase at a concentration of 10 U/mL to 50 U/mL, RNase inhibitor at a concentration of 200 U/mL to 1000 U/mL, mannitol at a concentration of 0.5% to 8%, sucrose at a concentration of 0.5% to 8%, bovine serum albumin at a concentration of 0.1 mg/mL to 1 mg/mL, polyoxyethylene lauryl ether at a concentration of 0.05%, HEPES at a concentration of 10 mmol/L to 50 mmol/L, and water. Applicant found that, through the combined use of the first and second components, the sample pyrolysis, the extraction of nucleic acid, and the preparation of fluorescent quantitative PCR reagents can be completed in absence of professionals, thereby reducing the technical requirements for operators, while providing excellent PCR amplification effect.

In another aspect of the present disclosure, the present disclosure provides a freeze-dried powder. According to an embodiment of the present disclosure, the freeze-dried powder is prepared from the composition described in any one of the above embodiments, and the freeze-dried powder is suitable for use in the method for performing a PCR reaction using a PCR reaction system and the PCR reaction system according to the above embodiments. Specifically, the freeze-dried powder can be provided in the sample containing unit. Applicant found that, when the first component and/or the second component are in the form of freeze-dried powder, the stability is greatly improved, and it can be stored and transported under normal temperature conditions, which greatly lowers the requirements on storage and transportation. The freeze-dried powder can be redissolved after being mixed with a suitable buffer, while the original functions can be maintained.

In addition, Applicant found that the existing sample pyrolysis diluent has a great difference from the PCR diluent in formula and composition. The sample pyrolysis diluent is specifically used for sample pyrolysis and nucleic acid extraction, while the PCR diluent is specifically used for PCR amplification, and these two diluents are not interchangably used. Based on the above problem, Applicant developed a diluent composition through a large number of experimental investigations, and this composition has the buffering effect in both the sample pyrolysis and PCR amplification reaction, so as to provide technical support for the integration of nucleic acid extraction and fluorescence PCR reaction of the sample.

Therefore, in another aspect of the present disclosure, the present disclosure provides a diluent. According to an embodiment of the present disclosure, the diluent includes: polyol, chloride salt, Tris-HCl, surfactant, and water. In some embodiments, the polyol is glycerol; the diluent is suitable for use in the method for performing a PCR reaction using a PCR reaction system and the PCR reaction system in the above-mentioned embodiments. Specifically, the diluent can be provided in the diluent containing unit. The diluent according to an embodiment of the present disclosure has a certain buffering effect on both the sample pyrolysis solution and the PCR reaction system. After the buffer dilution of the buffer solution, the lysate obtained after sample pyrolysis can be directly added to the PCR reaction system to complete the PCR reaction without purification, which provides technical support for the integration of nucleic acid extraction and PCR detection of the sample.

According to an embodiment of the present disclosure, the above-mentioned diluent may further include at least one of the following additional technical features.

According to an embodiment of the present disclosure, the surfactant includes at least one selected from the group consisting of Tween 20, Tween 80, polyethylene glycol octylphenol ether, sodium dodecyl sulfate (SDS), sodium dodecyl benzenesulfonate, sodium dioctyl sulfosuccinate, and sodium glycocholate.

According to an embodiment of the present disclosure, the chloride salt includes at least one selected from the group consisting of potassium chloride, sodium chloride, and magnesium chloride.

According to an embodiment of the present disclosure, the chloride is magnesium chloride and sodium chloride. Based on a total volume of the diluent, a concentration of the magnesium chloride ranges from 0.5 mmol/L to 15 mmol/L, for example, 1.0 mmol/L, 1.5 mmol/L, 2.0 mmol/L, 3.0 mmol/L, 5.0 mmol/L, 6.0 mmol/L, 8.0 mmol/L, 10.0 mmol/L, or 12.0 mmol/L; a concentration of the sodium chloride ranges from 1 mmol/L to 150 mmol/L, for example, 2 mmol/L, 4 mmol/L, 5 mmol/L, 10 mmol/L, 20 mmol/L, 40 mmol/L, 50 mmol/L, 60 mmol/L, 80 mmol/L, 100 mmol/L, or 120 mmol/L; a concentration of the surfactant ranges from 0.1% to 7%, for example, 0.1%, 0.2%, 0.4%, 0.5%, 1.0%, 2.0%, 3.0%, 4.0%, 5.0%, 6.0%, or 7.0%; a concentration of the glycerol ranges from 2% to 20%, for example, 3%, 5%, 7%, 8%, 9%, 12%, 15%, or 18%. It should be noted that, when the surfactant is a solid such as sodium dodecyl sulfate, the concentration of the surfactant is a mass volume concentration, i.e., the mass of the surfactant per 100 mL of solution, in unit of gram. For example, that the concentration of the sodium dodecyl sulfate ranges 0.1% to 7% indicates that the mass of the sodium dodecyl sulfate per 100 mL of the diluent ranges from 0.1 g to 7 g. When the surfactant is a liquid such as polyethylene glycol octylphenol ether or Tween 20, the concentration of the surfactant is a volume concentration, i.e., a volume of the surfactant per 100 mL of solution, in unit of milliliter. For example, that the concentration of the polyethylene glycol octylphenol ether or Tween 20 ranges from 0.1% to 7% indicates that the volume of the polyethylene glycol octylphenol ether or Tween 20 per 100 mL of the diluent ranges from 0.1 mL to 7 mL. In addition, that the concentration of glycerol is a volume concentration from 2% to 20% indicates that a volume of glycerol per 100 mL of the diluent ranges from 2 mL to 20 mL. Applicant found that, when the concentrations of respective ingredients in the diluent are within these ranges, the diluent can exert more effective buffering effect in both the sample pyrolysis and PCR amplification reaction.

According to an embodiment of the present disclosure, the chloride salt is magnesium chloride and sodium chloride, and based on the total volume of the diluent, the concentration of the magnesium chloride ranges from 1.5 mmol/L to 10 mmol/L, the concentration of the sodium chloride ranges from 5 mmol/L to 100 mmol/L, the concentration of the surfactant ranges from 0.1% to 5%, and the concentration of the glycerol ranges from 5% to 10%. Applicant found that, when the concentrations of respective ingredients in the diluent are within the above ranges, the diluent can exert more effective buffering effect in both the sample pyrolysis and PCR amplification reaction. Therefore, the diluent can also be used as a buffer for the PCR reaction.

According to an embodiment of the present disclosure, the Tris-HCl is provided in a form dissolved in water, i.e., an aqueous solution of Tris-HCl is added when preparing the diluent of the present disclosure. It should be noted that the aqueous solution of Tris-HCl is a type of buffer material commonly used in this field, which can be instantly prepared, e.g., adjusted slowly to preset pH using Tris base and hydrochloric acid, or directly purchased.

According to an embodiment of the present disclosure, the pH of the solution formed by dissolving Tris-HCl in water (the aqueous solution of Tris-HCl) ranges from 7.5 to 8.0, such as 7.6, 7.7, 7.8, 7.9, or 8.0. It should be noted that said pH does not refer to the pH of the diluent, but the pH of the solution formed by dissolving Tris-HCl in water. According to an embodiment of the present disclosure, when the pH of the solution formed by dissolving Tris-HCl in water ranges from 7.5 to 8.0, Tris-HCl has a better buffering effect on the diluent. In some embodiments, the pH of the solution formed by dissolving Tris-HCl in water is 7.6.

According to an embodiment of the present disclosure, based on the total volume of the diluent, the concentration of Tris-HCl ranges from 1 mmol/L to 100 mmol/L, for example, 3 mmol/L, 5 mmol/L, 7 mmol/L, 10 mmol/L, 20 mmol/L, 30 mmol/L, 40 mmol/L, 50 mmol/L, 70 mmol/L, 90 mmol/L, or 100 mmol/L. It should be noted that the concentration of Tris-HCl can be understood according to the common knowledge of those skilled in the art. According to an embodiment of the present disclosure, when the concentration of Tris-HCl ranges from 1 mmol/L to 100 mmol/L, the Tris-HCl has a better buffering effect on the diluent. In some embodiment, the concentration of Tris-HCl ranges from 5 mmol/L to 50 mmol/L.

In another aspect of the present disclosure, the present disclosure provides a diluent. According to an embodiment of the present disclosure, based on the total volume of the diluent, the diluent includes magnesium chloride at a concentration of 1.5 mmol/L to 10 mmol/L, sodium chloride at a concentration of 5 mmol/L to 100 mmol/L, and surfactant at a concentration of 0.1% to 5%, glycerol at a concentration of 5% to 10%, Tris-HCl at a concentration of 5 mmol/L to 50 mmol/L, and water. The surfactant is Tween 20, sodium dodecyl sulfate, or polyethylene glycol octylphenol ether. The diluent is applicable to the method for performing a PCR reaction using a PCR reaction system and the PCR reaction system in the above embodiment. Specifically, the diluent can be provided in the diluent containing unit. The diluent according to an embodiment of the present disclosure can exert more effective buffering effect in both the sample pyrolysis and PCR amplification reaction, and thus the diluent can also serve as a buffer for the PCR reaction.

BRIEF DESCRIPTION OF DRAWINGS

The accompanying drawings are used to provide a further understanding of the present disclosure and constitute a part of the specification. Together with the following specific embodiments, the accompanying drawings are intended to explain the present disclosure, but do not constitute a limitation on the present disclosure. In the accompanying drawings.

REFERENCE SIGNS

Figure 1:
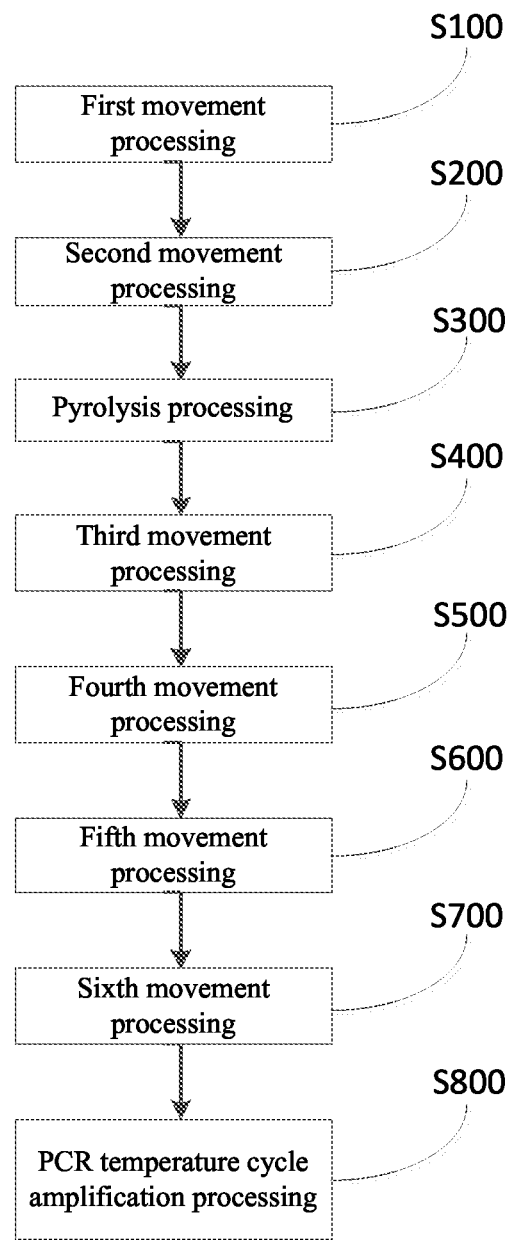
FIG. 1 is a schematic flowchart of a method for performing a PCR reaction using a PCR reaction system according to an embodiment of the present disclosure.

100: sample containing unit;
110: first liquid outlet/inlet;

200: diluent containing unit;
210: diluent outlet;
300: PCR reaction unit;
310: pyrolyzed sample mixture inlet;
320: PCR reaction solution outlet;
400: piston unit;
410: injection chamber;
411: second liquid outlet/inlet;
420: piston;
500: buffering unit;
510: PCR reaction solution inlet;
520: vent;
610: sample containing unit seal;
620: diluent containing unit seal;
710: piercing device for sample containing unit seal;
720: piercing device for sample containing unit seal;
810: sample control valve;
820: dilution control valve;
830: first PCR control valve;
840: second PCR control valve;
910: first pipeline;
920: second pipeline;
930: third pipeline;
940: fourth pipeline.

DESCRIPTION OF EMBODIMENTS

The embodiments of the present disclosure are described in detail below, and examples of the embodiments are illustrated in the accompanying drawings. The embodiments described below with reference to the drawings are exemplary, and are intended to explain the present disclosure, but should not be construed as limiting the present disclosure.

The present disclosure provides a method for performing a PCR reaction using a PCR reaction system and a corresponding PCR reaction system. According to an embodiment of the present disclosure, referring FIG. 5, the PCR reaction system includes: a sample containing unit 100, a diluent containing unit 200, a PCR reaction unit 300, and a piston unit 400. A pyrolysis freeze-dried powder and a sample are provided in the sample containing unit 100, and the sample containing unit 100 has a first liquid outlet/inlet 110. A diluent is provided in the diluent containing unit 200 and the diluent containing unit 200 has a diluent outlet 210. A freeze-dried powder of a reverse transcriptase and PCR raw materials is provided in the PCR reaction unit 300, the PCR reaction unit 300 is provided with a pyrolyzed sample mixture inlet 310 and a PCR reaction solution outlet 320, and the PCR reaction solution outlet 320 is connected to the diluent outlet 210 through a fourth pipeline 940. The piston unit includes an injection chamber 410 and a piston 420. The injection chamber 410 is provided with a second liquid outlet/inlet 411. The second liquid outlet/inlet 411 is connected to the first liquid outlet/inlet 110 through a first pipeline 910, the second liquid outlet/inlet 411 is connected to the diluent outlet 210 through a second pipeline 920, and the second liquid outlet/inlet 411 is connected to the pyrolyzed sample mixture inlet 310 through a third pipeline 930.

Referring to FIG. 1, the method includes: subjecting the piston 420 to a first movement processing S100, to allow a part of the diluent to enter the injection chamber 410, the diluent being provided in the diluent accommodating unit 200; subjecting the piston 420 to a second movement processing S200, to subject the part of the diluent entering the injection chamber 410, the pyrolysis freeze-dried powder, and the sample to a first mixing processing, where the pyrolysis freeze-dried powder and the sample are provided in the sample containing unit 100, and the first mixing processing is performed in the sample containing unit 100; subjecting a product of the first mixing processing to a pyrolysis processing S300, which is performed in the sample containing unit 100; subjecting the piston 420 to a third movement processing S400, to allow a product of the pyrolysis processing to enter the injection chamber 410; subjecting the piston 420 to a fourth movement processing S500, to subject the product of the pyrolysis processing entering the injection chamber 410 and the remaining part of the diluent to a second mixing processing, which is performed in the diluent containing unit 200; subjecting the piston 420 to a fifth movement processing S600, to allow a product of the second mixing processing to enter the injection chamber 410; subjecting the piston 420 to a sixth movement processing S700, to subject the product of the second mixing processing entering the injection chamber 410 and the freeze-dried powder of the reverse transcriptase and the PCR raw materials to a third mixing processing, where the freeze-dried powder of the reverse transcriptase and the PCR raw materials is provided in the PCR reaction unit 300, and the third mixing processing is performed in the PCR reaction unit 300; and subjecting a product of the third mixing processing to a PCR temperature cycle amplification processing S800, which is performed in the PCR reaction unit 300.

Figure 5:
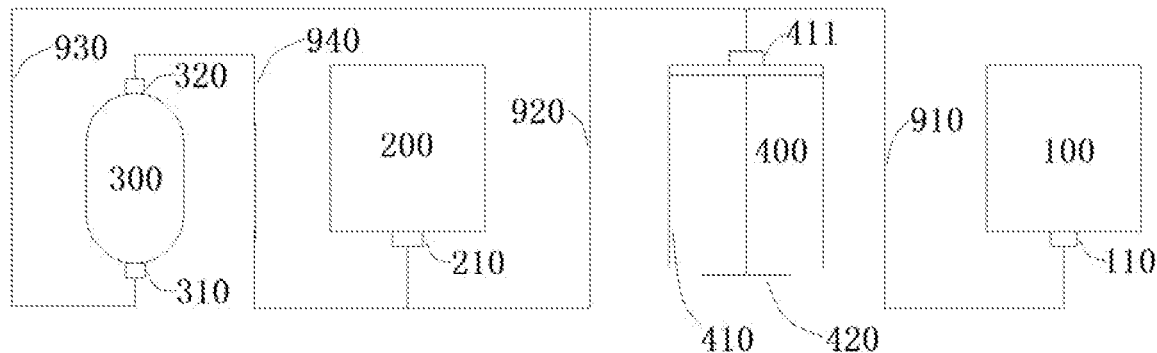
FIG. 5 is a schematic structural diagram of a PCR system according to an embodiment of the present disclosure.

In the PCR reaction system according to embodiment of the present disclosure, the sample containing unit 100, the diluent containing unit 200, the PCR reaction unit 300, and the piston unit 400 are connected to each other through the microfluidic pipelines; and at the same time, respective units are independently set units, such that the respective units store different reactants before use, which is conducive to long-term storage of reactants when not in use. For example, the independent setting of the sample containing unit 100 is conducive to separately adding samples, thereby simplifying the operation of adding samples, and also facilitating the long-term storage of samples. Referring to FIG. 1 and FIG. 5, the piston 420 is first pulled outward to a certain position, to allow a part of the diluent in the diluent containing unit 200 to flow to the injection chamber 410; then the piston 420 is moved back and forth to allow the diluent in the injection chamber 410 to enter the sample containing unit 100, and to be mixed evenly with the pyrolysis freeze-dried powder and the sample in the sample containing unit 100 at the same time; then the sample containing unit 100 is heated to a set temperature, so that the sample in the sample containing unit 100 is fully pyrolyzed at the set temperature; after the pyrolysis is completed, the piston 420 is pulled outward again to a certain position, allowing the pyrolyzed sample mixture in the sample containing unit 100 to flow to the injection chamber 410; then the piston 420 is moved back and forth to return, such that the pyrolyzed sample mixture in the injection chamber 410 returns to the diluent containing unit 200 and is mixed evenly with the remaining diluent in the diluent containing unit 200 at the same time, thereby diluting the pyrolyzed sample mixture and reducing a concentration of impurities therein; afterwards, the piston 420 is pulled outward again to a certain position, to allow the diluted sample mixture in the diluent containing unit 200 to flow to the injection chamber 410; then the piston 420 is moved back and forth, such that the diluted sample mixture in the injection chamber 410 enters the PCR reaction unit 300 and is mixed evenly with the freeze-dried powder of the reverse transcriptase and the PCR raw materials in the PCR reaction unit 300 at the same time; and finally, the PCR reaction unit 300 is subjected to a PCR temperature increasing control, so as to complete the PCR amplification reaction. In the PCR reaction system according to embodiment of the present disclosure, the PCR reaction solution outlet is connected to the diluent outlet through the fourth pipeline to form a pressure system connection between the PCR reaction solution outlet and the diluent outlet, such that the excess reaction liquid in the PCR reaction unit can smoothly flow out to the fourth pipeline through the reaction liquid outlet. Further, in the PCR reaction system according to embodiment of the present disclosure, valves or other switches can be flexibly designed at appropriate positions of the microfluidic pipelines to control a connection state between piston unit 400 and the sample containing unit 100, the diluent containing unit 200, or the PCR reaction unit 300. In addition, the movement of the piston and the control of respective valves or other switches can also be flexibly designed together with other mechanical devices to achieve automation. In the PCR reaction method according to the embodiment of the present disclosure, the pyrolyzed sample mixture is returned to the diluent containing unit and mixed evenly with the remaining part of the diluent in the diluent containing unit. In this way, the pyrolyzed sample mixture can be diluted and the concentration of impurities therein can be significantly lowered, so as to prevent the impurities generated after lysis from adversely affecting the subsequent PCR amplification reaction, which is conducive to the automation of the PCR reaction. It should be noted that those skilled in the art can design the specific dosage ratio of the two parts of the diluent according to actual needs. As a result, the PCR reaction method according to the embodiment of the present disclosure achieves a fully automatic process from sample nucleic acid extraction to mixing with reagents, and finally to PCR reaction, which solves the tricky problem that the conventional PCR experiment process needs to be operated by professionals in a professional experimental environment. The method can be performed in absence of the professionals and reduces the manual errors, significantly improving the working efficiency of the PCR reaction, and greatly saving the cost of human resources.

The method according to the embodiment of the present disclosure is described in detail below with reference to the drawings.

Figure 2:
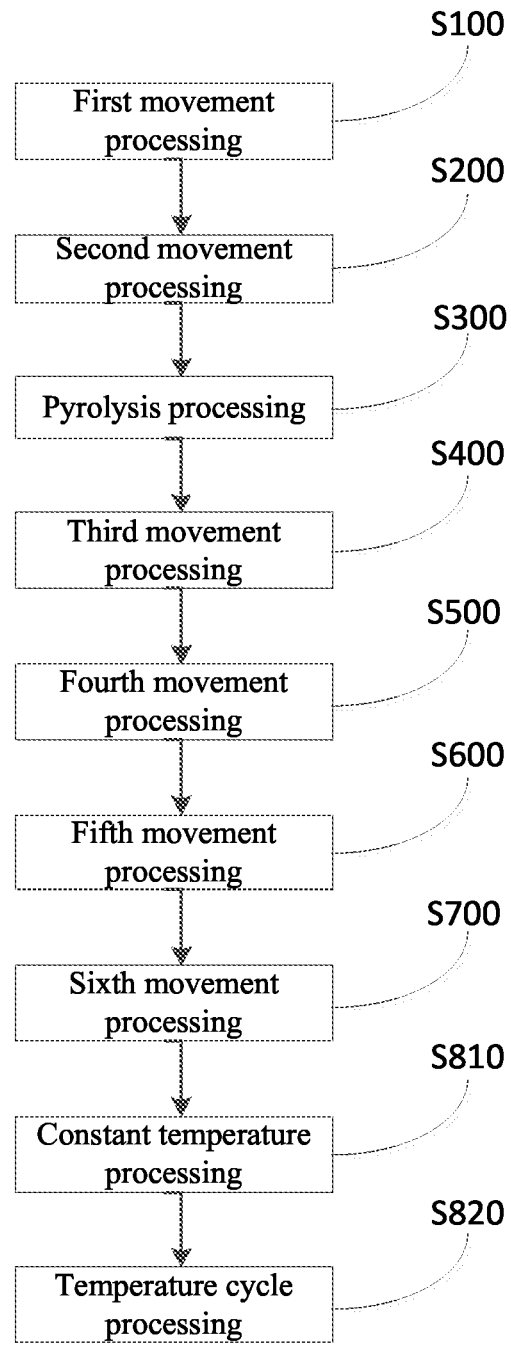
FIG. 2 is a schematic flowchart of a method for performing a PCR reaction using a PCR reaction system according to another embodiment of the present disclosure.

According to another embodiment of the present disclosure, referring to FIG. 2, the PCR temperature cycle amplification processing S800 includes: subjecting the product of the third mixing processing to a constant temperature processing S810; and subjecting a product of the constant temperature processing to a temperature cycle processing S820.

Figure 6:
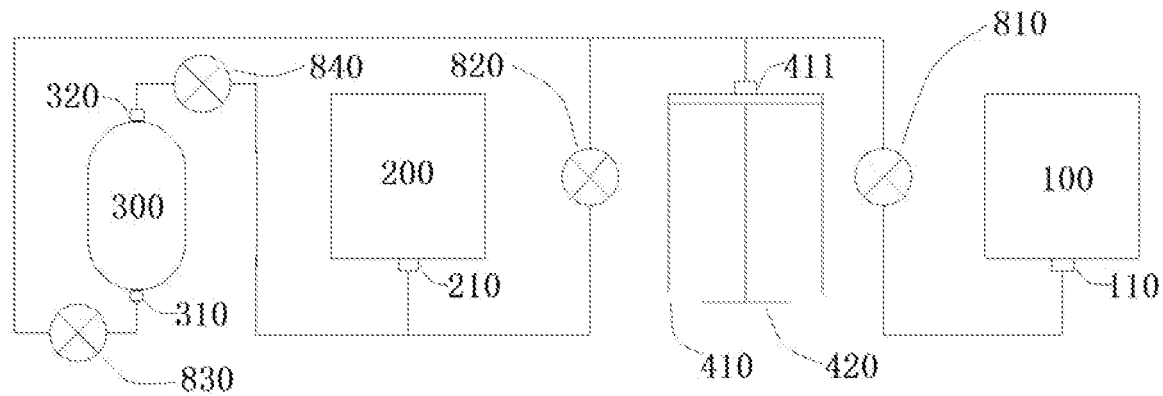
FIG. 6 is a schematic structural diagram of a PCR system according to another embodiment of the present disclosure.

According to another embodiment of the present disclosure, referring to FIG. 6, the PCR reaction system further includes: a sample control valve 810, which is provided on the first pipeline 910 and configured to control a connection state between the second liquid outlet/inlet 411 and the first liquid outlet/inlet 110; a dilution control valve 820, which is provided on the second pipeline 920 and configured to control a connection state between the second liquid outlet/inlet 411 and the diluent outlet 210; a first PCR control valve 830, which is provided on the third pipeline 930 and configured to control a connection state between the second liquid outlet/inlet 411 and the pyrolyzed sample mixture inlet 310; and a second PCR control valve 840, which is provided on the fourth pipeline 940 and configured to control a connection state between the PCR reaction solution outlet 320 and the diluent outlet 210.

Figure 3:
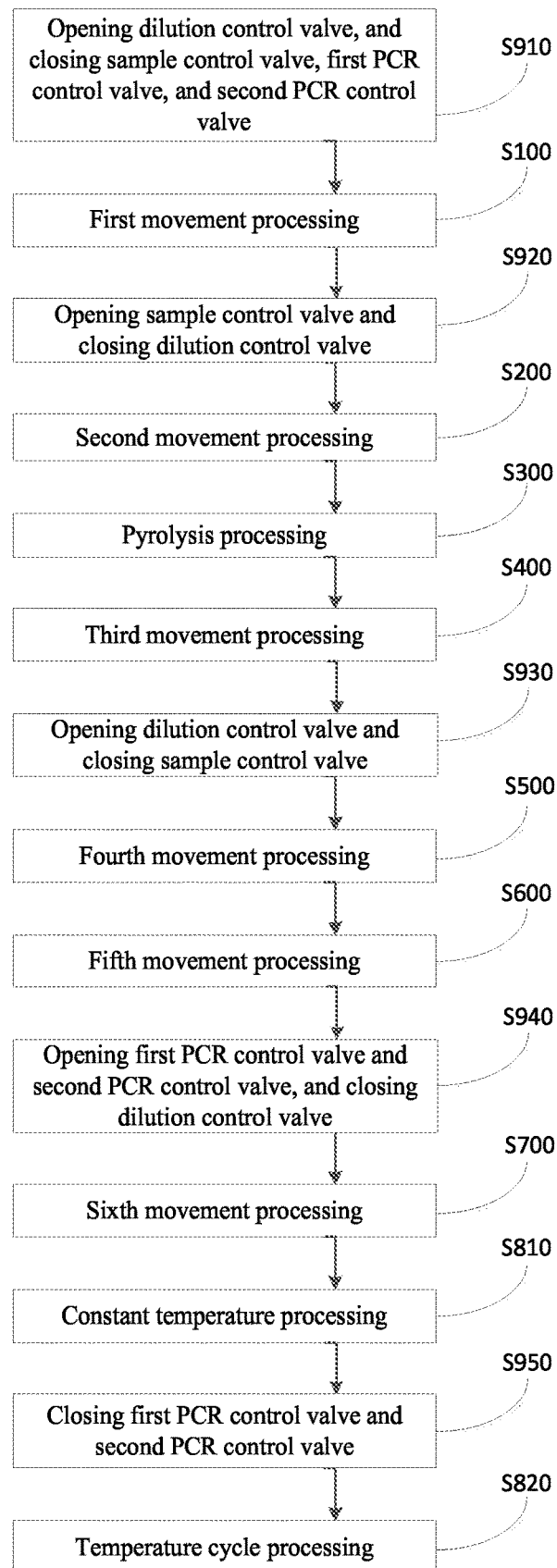
FIG. 3 is a schematic flowchart of a method for performing a PCR reaction using a PCR reaction system according to yet another embodiment of the present disclosure.

Referring to FIG. 3, the method further includes: S910: prior to the first movement processing, closing the sample control valve, the first PCR control valve, and the second PCR control valve, and opening the dilution control valve; S920: subsequent to the first movement processing and prior to the second movement processing, closing the dilution control valve and opening the sample control valve; S930: subsequent to the third movement processing and prior to the fourth movement processing, closing the sample control valve and opening the dilution control valve; S940: subsequent to the fifth movement processing and prior to the sixth movement processing, closing the dilution control valve, and opening the first PCR control valve and the second PCR control valve; and S950: subsequent to the constant temperature processing and prior to the temperature cycle processing, closing the first PCR control valve and the second PCR control valve.

According to an embodiment of the present disclosure, referring to FIG. 3 and FIG. 6, first, the first PCR control valve 830, the second PCR control valve 840, and the sample control valve 810 are closed, and the dilution control valve 820 is opened; then, the piston 420 is pulled outward to a certain position, to allow a part of the diluent in the diluent containing unit 200 to flow to the injection chamber 410; afterwards, the dilution control valve 820 is closed and the sample control valve 810 is opened; then the piston 420 is moved back and forth to allow the diluent in the injection chamber 410 to enter the sample containing unit 100 and to be mixed evenly with the pyrolysis freeze-dried powder and the sample in the sample containing unit 100 at the same time; then the sample containing unit 100 is heated to a set temperature, so that the sample in the sample containing unit 100 is fully pyrolyzed at the set temperature; after the pyrolysis is completed, the piston 420 is pulled outward again to a certain position, allowing the pyrolyzed sample mixture in the sample containing unit 100 to flow to the injection chamber 410; afterwards, the sample control valve 810 is closed, and the dilution control valve 820 is opened; then the piston 420 is moved back and forth, such that the pyrolyzed sample mixture in the injection chamber 410 returns to the diluent containing unit 200 and is mixed evenly with the remaining diluent in the diluent containing unit 200 at the same time, thereby diluting the pyrolyzed sample mixture and reducing a concentration of impurities therein; afterwards, the piston 420 is pulled outward again to a certain position, to allow the diluted sample mixture in the diluent containing unit 200 to flow to the injection chamber 410; afterwards, the dilution control valve 820 is closed, and the first PCR control valve 830 and the second PCR control valve 840 are opened; then the piston 420 is moved back and forth, such that the diluted sample mixture in the injection chamber 410 enters the PCR reaction unit 300 and is mixed evenly with the freeze-dried powder of the reverse transcriptase and the PCR raw materials in the PCR reaction unit 300 at the same time; and finally, the PCR reaction unit 300 is subjected to the PCR temperature increasing control. The PCR temperature increasing control includes an early-stage constant temperature phase for activating enzyme and a temperature cycle control phase. Before the temperature cycle control is performed, the first PCR control valve 830 and the second PCR control valve 840 are closed, so as to finally complete the PCR amplification reaction. In the PCR reaction system according to the embodiment of the present disclosure, the respective units and valves perfectly cooperate and work synergistically to reduce the pollution of the experimental products to the environment as well as the pollution of the environment to the experimental process, which is conducive to achieving full automation, in absence of professionals for manual operation. Therefore, the PCR reaction method according to the embodiment of the present disclosure is performed in a sealed environment, which reduces the pollution to the system environment and improves the credibility of the experiment, and the operation is more convenient and easier to implement.

Figure 7:
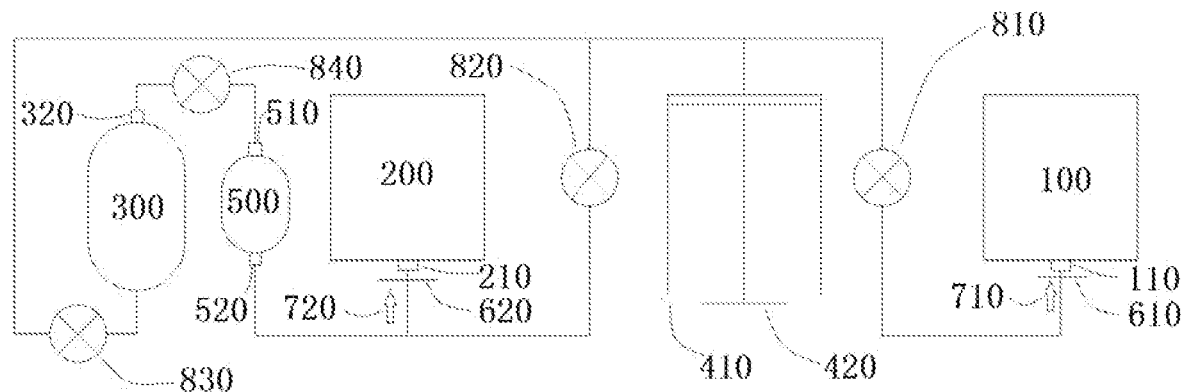
FIG. 7 is a schematic structural diagram of a PCR system according to yet another embodiment of the present disclosure.

According to another embodiment of the present disclosure, referring to FIG. 3 and FIG. 7, the PCR reaction system further includes a buffering unit 500. The buffering unit 500 is provided with a PCR reaction solution inlet 510 and a vent 520. The buffering unit 500 is provide on the fourth pipeline 940. The PCR reaction solution inlet 510 is connected to the second PCR control valve 840, and the vent 520 is connected to the diluent outlet 210.

According to an embodiment of the present disclosure, referring to FIG. 3 and FIG. 7, first, the first PCR control valve 830, the second PCR control valve 840, and the sample control valve 810 are closed, and the dilution control valve 820 is opened; then, the piston 420 is pulled outward to a certain position, to allow a part of the diluent in the diluent containing unit 200 to flow to the injection chamber 410; afterwards, the dilution control valve 820 is closed and the sample control valve 810 is opened; then the piston 420 is moved back and forth to allow the diluent in the injection chamber 410 to enter the sample containing unit 100 and to be mixed evenly with the pyrolysis freeze-dried powder and the sample in the sample containing unit 100 at the same time; then the sample containing unit 100 is heated to a set temperature, so that the sample in the sample containing unit 100 is fully pyrolyzed at the set temperature; after the pyrolysis is completed, the piston 420 is pulled outward again to a certain position, allowing the pyrolyzed sample mixture in the sample containing unit 100 to flow to the injection chamber 410; afterwards, the sample control valve 810 is closed, and the dilution control valve 820 is opened; then the piston 420 is moved back and forth, such that the pyrolyzed sample mixture in the injection chamber 410 returns to the diluent containing unit 200 and is mixed evenly with the remaining diluent in the diluent containing unit 200 at the same time, thereby diluting the pyrolyzed sample mixture and reducing a concentration of impurities therein; afterwards, the piston 420 is pulled outward again to a certain position, to allow the diluted sample mixture in the diluent containing unit 200 to flow to the injection chamber 410; afterwards, the dilution control valve 820 is closed, and the first PCR control valve 830 and the second PCR control valve 840 are opened; then the piston 420 is moved back and forth, such that the diluted sample mixture in the injection chamber 410 enters the PCR reaction unit 300 and is mixed evenly with the freeze-dried powder of the reverse transcriptase and the PCR raw materials in the PCR reaction unit 300 at the same time; and finally, the PCR reaction unit 300 is subjected to a PCR temperature increasing control. In the early-stage constant temperature phase for the enzyme activation in PCR amplification, the mixture in the PCR reaction unit 300 may expand due to high temperature, and the liquid overflowing during the expansion process may flow into the buffering unit 500. After the constant temperature phase is over, the first PCR control valve 830 and the second PCR control valve 840 are closed to perform the temperature cycle control on the PCR reaction unit 300, so as to finally complete the PCR amplification reaction. Therefore, the PCR reaction method according to the embodiment of the present disclosure can solve the overflow problem of PCR reagents during high temperature expansion, and the PCR reaction is carried out in a sealed environment, which reduces the pollution to the system environment and improves the credibility of the experiment, and the operation is more convenient and easier to implement.

According to another embodiment of the present disclosure, referring to FIG. 7, the PCR reaction system further includes a sample containing unit seal 610 and a diluent containing unit seal 620. The sample containing unit seal 610 is provided on a surface of the first liquid outlet/inlet 110 for use in a first sealing processing of the sample containing unit 100. The diluent containing unit seal 620 is provided on a surface of the diluent outlet 210 for use in a second sealing processing of the diluent containing unit 200.

Figure 4:
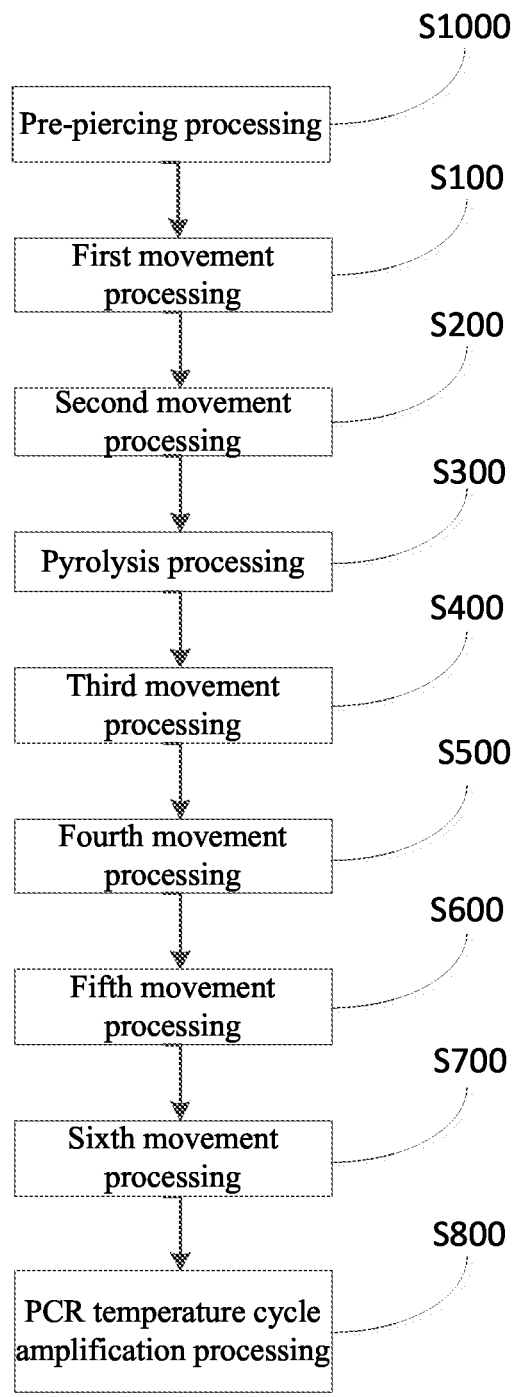
FIG. 4 is a schematic flowchart of a method for performing a PCR reaction using a PCR reaction system according to yet another embodiment of the present disclosure.

Referring to FIG. 4, the method further includes a pre-piercing processing S1000. The pre-piercing processing includes subjecting the sample containing unit seal to a first piercing processing in advance, and subjecting the diluent containing unit seal to a second piercing processing in advance.

According to an embodiment of the present disclosure, referring to FIG. 4 and FIG. 7, in an initial state, the sample containing unit 100 contains the pyrolysis raw material in the form of freeze-dried powder, the PCR reaction unit 300 contains the reverse transcriptase and PCR raw materials in the form of freeze-dried powder, and the diluent containing unit 200 contains an appropriate diluent. The connections between the sample containing unit 100 and the microfluidic pipeline, and between the diluent containing unit 200 and the microfluidic pipeline are respectively sealed with the sample containing unit seal 610 and the diluent containing unit seal 620, so that the pyrolysis raw material of the sample containing unit 100, the diluent of the diluent containing unit 200, as well as the reverse transcriptase and the PCR raw materials in the PCR reaction unit 300 are isolated from each other, and the piston 420 is at the top of the injection chamber 410 (i.e., the injection chamber is in a state of being fully filled by the piston). It should be noted that under the premise that the PCR reaction system includes the sample containing unit seal and the diluent containing unit seal, the respective units can be isolated from each other without a PCR reaction sealing device, and even if a small amount of reactants in the PCR reaction unit enters the pipelines, it has little effect on the overall reaction. The sample containing unit seal and the diluent containing unit seal can not only isolate the reactants in respective independent units, facilitate long-term storage when not in use, greatly increase the storage time of respective reactants in the respective units, but also can avoid the contamination of the PCR reaction system caused by the reactants and increase the service life of the PCR reaction system. Furthermore, when the sample containing unit is added with the sample, the sample containing unit and the diluent containing unit can be in connection state with the microfluidic pipelines only by piercing the sample containing unit seal and the diluent containing unit seal, and thus the system can start working. In this way, the method according to the embodiment of the present disclosure is more convenient in the operation.

According to an embodiment of the present disclosure, referring to FIG. 4 and FIG. 7, the first piercing processing is performed by a piercing device 710 for the sample containing unit seal, and the second piercing process is performed by a piercing device 720 for the diluent containing unit seal.

According to an embodiment of the present disclosure, at least one of the sample containing unit seal and the diluent containing unit seal is a sealing film.

According to an embodiment of the present disclosure, the sealing film is formed of at least one of a tin foil paper, a laminating film, or a kraft paper.

According to an embodiment of the present disclosure, the sealing film has a thickness ranging from 0.01 mm to 0.2 mm, for example, 0.03 mm, 0.05 mm, 0.07 mm, 0.09 mm, 0.1 mm, 0.13 mm, 0.15 mm, 0.17 mm, or 0.19 mm. Applicant found that if the sealing film is too thin, it may be permeable, but if the sealing film is too thick, it will be difficult to be pierced. In some embodiments, the thickness of the sealing film ranges from 0.05 mm to 0.1 mm.

The method for performing a PCR reaction using a PCR reaction system and the PCR reaction system of the present disclosure are further described by means of the following specific examples.

Example 1

Structure of the System:

Referring to FIG. 7, a structure of the system includes: a sample containing unit 100 designed as a sample chamber, a diluent containing unit 200 designed as a dilution chamber, an injection chamber 410, a piston 420, a PCR reaction unit 300 designed as a PCR chamber, a buffering unit 500 designed as a buffering chamber, a sample containing unit seal 610 designed as a sample sealing film, a diluent containing unit seal 620 designed as a dilution sealing film, microfluidic pipelines, a sample control valve 810, a dilution control valve 820, a first PCR control valve 830, and a second PCR control valve 840. The respective units are connected by the microfluidic pipelines to form an associated circuit.

Working Principle of the System:

Referring to FIG. 7, in the initial state, the sample chamber contains the pyrolysis raw material in the form of freeze-dried powder, the PCR chamber contains the reverse transcriptase and the PCR raw materials in the form of freeze-dried powder, and the dilution chamber contains an appropriate diluent. Connections between the sample chamber and the microfluidic pipeline and between the diluent chamber and the microfluidic pipeline are respectively sealed with the sample sealing film and the dilution sealing film, so that the pyrolysis raw material of the sample chamber, the diluent of the diluent chamber, as well as the reverse transcriptase and the PCR raw materials in the PCR chamber are isolated from each other. The piston is at the top of the injection chamber (the injection chamber is in a state of being fully filled by the piston).

When a sample is added to the sample chamber, the system starts working. Firstly, the sample sealing film and the dilution sealing film are pierced by the piercing devices 710/720, enabling a connection state between the units and the microfluidic pipelines. Secondly, the sample control valve, the first PCR control valve, and the second PCR control valve are closed, and the piston is moved and pulled outward to a certain position, so that the diluent in the dilution chamber flows to the injection chamber through the dilution control valve. Thirdly, the dilution control valve is closed, the sample control valve is opened, the piston is moved back and forth, allowing the part of the diluent in the injection chamber to enter the sample chamber through the sample control valve. During the back and forth movement of the piston, the pyrolysis freeze-dried powder in the sample chamber is evenly mixed with the diluent and the added sample. Fourthly, the sample chamber is heated to a set temperature, allowing the sample in the sample chamber is fully pyrolyzed at the set temperature. Fifthly, after the pyrolysis is completed, the piston is moved and pulled outward again to a certain position, so as to allow the pyrolyzed sample mixture in the sample chamber to flow to the injection chamber through the sample control valve. Sixthly, the sample control valve is closed, the dilution control valve is opened, the piston is moved back and forth, such that the pyrolyzed sample mixture in the injection chamber returns to the dilution chamber, and is sufficiently and evenly mixed with the remaining diluent in the dilution chamber under the back and forth movement of the piston, thereby diluting the pyrolyzed sample mixture and reducing a concentration of impurities therein. Seventhly, the piston is pulled outward again to a certain position, to allow the diluted sample mixture in the dilution chamber to flow to the injection chamber. Eighthly, the dilution control valve is closed, the first PCR control valve and the second PCR control valve are opened, and the piston is moved back and forth, such that the sample mixture in the injection chamber enters the PCR chamber through the PCR control valve, and is sufficiently and evenly mixed with the freeze-dried powder of the reverse transcriptase and the PCR raw materials in the PCR chamber under the back and forth movement of the piston. Ninthly, the PCR chamber is subjected to a PCR temperature increasing control. In an early-stage constant temperature phase for the enzyme activation in PCR amplification, the mixture in the PCR chamber may expand due to high temperature, and the liquid overflowing during the expansion process may flow into the buffering chamber through the second PCR control valve. After the constant temperature phase is over, the first PCR control valve and the second PCR control valve are closed to perform the temperature cycle control on the PCR chamber, so as to finally complete the PCR amplification reaction.

The composition and the freeze-dried powder of the above-mentioned PCR reaction are described in detail below. It should be noted that, unless otherwise specified, the meanings of respective components and concentrations in the present disclosure can be understood according to conventional interpretations in the field, such as EDTA and EGTA. In addition, Amplification Plot represents an amplification curve, and Cycle represents the number of cycles. It should also be noted that, except that the compositions or freeze-dried powder of the present disclosure for the sample pyrolysis and nucleic acid extraction are Applicant's research and development results, unless otherwise specified, other relevant reagents used in the following steps can be obtained by purchasing or consulting existing technology. Those skilled in the art can be purchased or obtained by referring to the prior art. Those skilled in the art can purchase relevant reagents according to the actual needs, or consult the prior art to obtain relevant reagents.

I. Preparation of Freeze-Dried Powder for Sample Pyrolysis and Nucleic Acid Extraction 1. Certain amounts of target ingredients were weighed or aspirated to prepare a predetermined volume of mixed solution. In the mixed solution, EDTA was 0.5 mM to 5 mM, EGTA was 0.5 mM to 10 mM, sodium dodecyl sulfate was 0.5% to 2.5%, saponin was 0.5% to 2.5%, proteinase K was 10 U/mL to 100 U/mL, polyethylene glycol 3350 was 0.5% to 4.5%, Tris-HCl was 5 mM to 20 mM, water was added to the predetermined volume, and the pH of the aspirated Tris-HCl solution was 7.5 to 8.2.

2. 50 μL of the above mixed solution was aspirated and freeze-dried according to a conventional freeze-drying method (such as freeze-drying on dry ice, placing in a freeze dryer, and drying and sublimating at −30° C.) to prepare a certain amount of freeze-dried powder for the sample pyrolysis and nucleic acid extraction.

II. Preparation of the Freeze-Dried Powder of Fluorescence Quantitative PCR Reagent 1. Certain amount of target ingredients were weighed and aspirated to prepare a predetermined volume of mixed solution. In the mixed solution, mannitol was 0.5% to 8%, sucrose was 0.5% to 8%, potassium chloride was 20 mM to 100 mM, magnesium chloride was 1.0 mM to 5 mM, bovine serum albumin was 0.1 mg/mL to 1 mg/mL, dNTPs was 200 µM, Brij 35 was 0.05%, HEPES was 10 mM to 50 mM, DNA polymerase was 20 U/mL to 200 U/mL, M-MLV reverse transcriptase was 10 U/mL to 50 U/mL, the RNase inhibitor was 200 U/mL to 1000 U/mL, and water was added to the predetermined volume, and the pH of the aspirated HEPES solution was 8.0 to 8.5.

2. The above-mentioned mixed solution was filtered and freeze-dried according to a conventional freeze-drying method to prepare and obtain a certain amount of the freeze-dried powder of the fluorescent quantitative PCR reagent.

III. Property Test

1) Toxicity

The ingredients for preparing the freeze-dried powder for the sample pyrolysis and nucleic acid extraction did not contain toxic substances such as phenol, chloroform, guanidine hydrochloride, or guanidine isothiocyanate, and thus had low toxicity.

2) Stability

The freeze-dried powder of fluorescence quantitative PCR reagent was stored at room temperature and had good stability.

3) Sample Pyrolysis and Nucleic Acid Extraction, and Fluorescence Quantitative PCR Verification Test Sample Pyrolysis:

Influenza A virus (Flu A) was added to the pyrolysis solution in a certain proportion, and incubated at 95° C. for a certain period of time for sample pyrolysis.

Fluorescence Quantitative PCR Verification Test:

The above pyrolyzed sample was added to a redissolved fluorescent quantitative PCR reaction system in a certain proportion, and corresponding Flu A primers and probes were added. The fluorescence quantitative PCR reaction was performed, and the reaction procedure was as follows: 50° C., 5 min; 95° C., 2 min; 95° C., 15 s, 60° C., 1 min, 40 Cycles. The sequences of the primers and probes are as follows:

```
FluA-Forward:
                                  (SEQ ID NO: 1)
CAGAGACTTGAAGATGTTTTGC FluA-Reverse:
                                  (SEQ ID NO: 2)
CTACGCTGCAGTCCTCGCTC FluA-Prob:
                                  (SEQ ID NO: 3)
CY3-CAAGACCAATCCTGTCACCTCTGA-BHQ2
```

Example 2

1. Preparation of Freeze-Dried Powder for Sample Pyrolysis and Nucleic Acid Extraction Certain amounts of target ingredients were weighed or aspirated to prepare a predetermined volume of mixed solution. In the mixed solution, EDTA was 2 mM, EGTA was 2 mM, sodium dodecyl sulfate was 1%, saponin was 1.0%, proteinase K was 20 U/mL, polyethylene glycol 3350 was 1%, Tris-HCl was 10 mM, water was added to the predetermined volume, and the pH of the aspirated Tris-HCl solution was 7.6.

50 µL of the above mixed solution was aspirated and added to an 8-connected tube, centrifuged and precipitated to the bottom of the tube, and stored at −80° C. to freeze overnight, following by taking out and placing in a freeze dryer for freeze drying overnight. The lid was closed after the freeze drying, and the tube was stored at room temperature. It was ensured that the temperature of the freeze dryer was below −45° C., the vacuum pressure was lower than 450 Torr, and the sample in the test tube was placed on dry ice for at least 30 minutes.

2. Preparation of the Freeze-Dried Powder of Fluorescence Quantitative PCR Reagent Certain amounts of target ingredients were weighed and aspirated to prepare a predetermined volume of mixed solution. In the mixed solution, mannitol was 1.5%, sucrose was 1.5%, potassium chloride was 80 mM, magnesium chloride was 3.5 mM, bovine serum albumin was 0.5 mg/mL, dNTPs was 200 µM, Brij 35 was 0.05%, HEPES was 20 mM, DNA polymerase was 40 U/mL, M-MLV reverse transcriptase was 20 U/mL, the RNase inhibitor was 500 U/mL, and water was added to the predetermined volume, and the pH of the aspirated HEPES solution was 8.25.

18 µL of the above mixed solution was aspirated and added to an 8-connected tube, centrifuged and precipitated to the bottom of the tube, and stored at −80° C. to freeze overnight, following by taking out and placing in a freeze dryer for freeze drying overnight. The lid was closed after the freeze drying, and the tube was stored at room temperature. It was ensured that the temperature of the freeze dryer was below −45° C., the vacuum pressure was lower than 450 Torr, and the sample in the test tube was placed on dry ice for at least 30 minutes.

3. Sample Pyrolysis and Nucleic Acid Extraction, and Fluorescence Quantitative PCR Verification Test The preparation and freeze-drying of the reagents for the sample pyrolysis and nucleic acid extraction, as well as the fluorescent quantitative PCR are performed according to the above methods. After being stored at room temperature for 3 months, the freeze-dried powder was redissolved by adding water, and then the Flu A virus was added for the sample pyrolysis. Then, the pyrolyzed sample was added to the redissolved fluorescent quantitative PCR reaction system in the abovementioned proportion added with Flu A primers and probes, and the fluorescence quantitative PCR verification test was performed. The test results are illustrated in FIG. 8.

Figure 8:
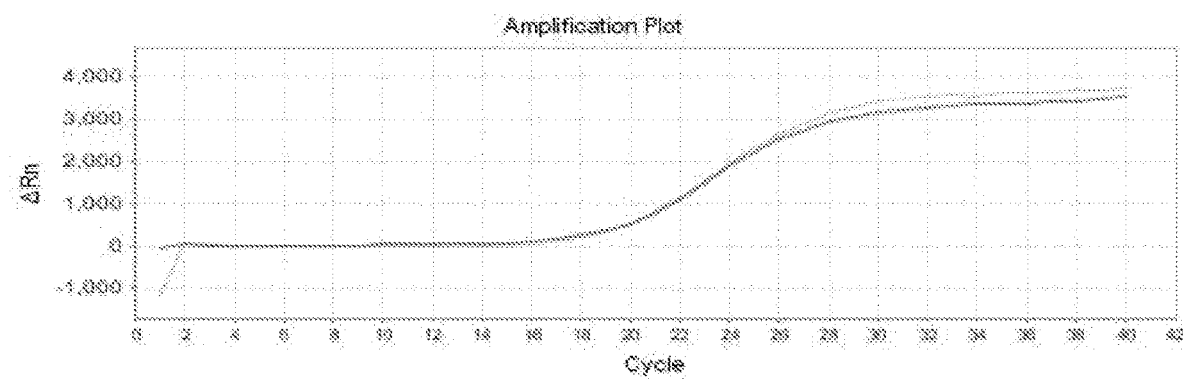
FIG. 8 is a schematic diagram of test results of Example 2 of the present disclosure.

Conclusion: it can be seen from FIG. 8 that, the freeze-dried powder reagent, after being stored at room temperature for 3 months, was redissolved and can still be normally used for amplification. It indicates that the reagent formulations of the first component and the second component can be redissolved after being freeze-dried and still maintain the pyrolysis and PCR detection activity of the sample.

Example 3

1. Preparation of Freeze-Dried Powder for Sample Pyrolysis and Nucleic Acid Extraction Certain amounts of target ingredients were weighed or aspirated to prepare a predetermined volume of mixed solution. In the mixed solution, EDTA was 4 mM, EGTA was 4 mM, sodium dodecyl sulfate was 2%, saponin was 2%, proteinase K was 80 U/mL, polyethylene glycol 3350 was 4%, Tris-HCl was 18 mM, water was added to the predetermined volume, and the pH of the aspirated Tris-HCl solution was 7.6.

50 μL of the above mixed solution was aspirated and added to an 8-connected tube, centrifuged and precipitated to the bottom of the tube, and stored at −80° C. to freeze overnight, following by taking out and placing in a freeze dryer for freeze drying overnight. The lid was closed after the freeze drying, and the tube was stored at room temperature. It was ensured that the temperature of the freeze dryer was below −45° C., the vacuum pressure was lower than 450 Torr, and the sample in the test tube was placed on dry ice for at least 30 minutes.

2. Preparation of the Freeze-Dried Powder of Fluorescence Quantitative PCR Reagent Certain amounts of target ingredients were weighed and aspirated to prepare a predetermined volume of mixed solution. In the mixed solution, mannitol was 6%, sucrose was 3%, potassium chloride was 40 mM, magnesium chloride was 5 mM, bovine serum albumin was 1 mg/mL, dNTPs was 200 μM, Brij 35 was 0.05%, HEPES was 40 mM, DNA polymerase was 100 U/mL, M-MLV reverse transcriptase was 40 U/mL, the RNase inhibitor was 800 U/mL, and water was added to the predetermined volume, and the pH of the aspirated HEPES solution was 8.25.

18 μL of the above mixed solution was aspirated and added to an 8-connected tube, centrifuged and precipitated to the bottom of the tube, and stored at −80° C. to freeze overnight, following by taking out and placing in a freeze dryer for freeze drying overnight. The lid was closed after the freeze drying, and the tube was stored at room temperature. It was ensured that the temperature of the freeze dryer was below −45° C., the vacuum pressure was lower than 450 Torr, and the sample in the test tube was placed on dry ice for at least 30 minutes.

Figure 9:
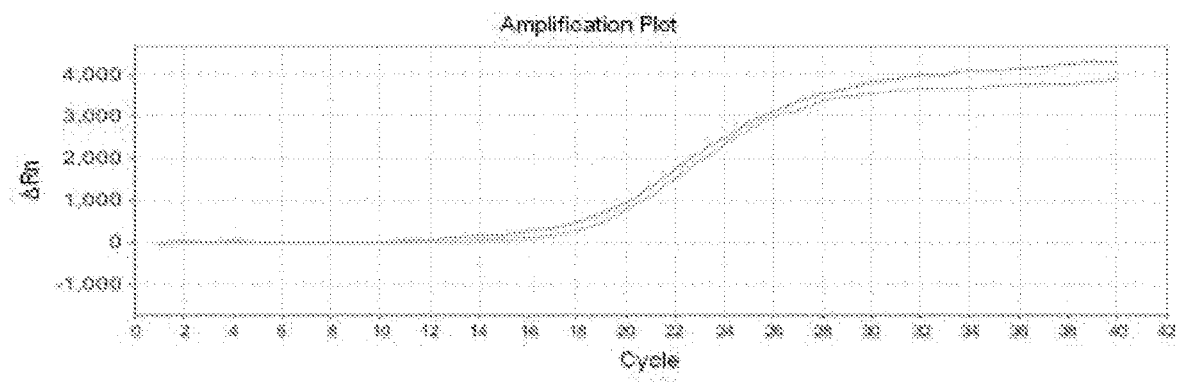
FIG. 9 is a schematic diagram of test results of Example 3 of the present disclosure.

3. Sample Pyrolysis and Nucleic Acid Extraction, and Fluorescence Quantitative PCR Verification Test The preparation and freeze-drying of the reagents for the sample pyrolysis and nucleic acid extraction, as well as the fluorescent quantitative PCR are performed according to the above methods. After being stored at room temperature for 3 months, the pyrolyzed sample was redissolved by adding water, and then the Flu A virus was added for the sample pyrolysis. Then, the pyrolyzed sample was added to the redissolved fluorescent quantitative PCR reaction system in the abovementioned proportion added with Flu A primers and probes, and the fluorescence quantitative PCR verification test was performed. The test results are illustrated in FIG. 9.

Conclusion: It can be seen from FIG. 9 that, the freeze-dried powder reagent, after being stored at room temperature for 3 months, was redissolved and can still be normally used for amplification. It indicates that the reagent formulations of the first component and the second component can be redissolved after being freeze-dried and still maintain the pyrolysis and PCR detection activity of the sample.

Comparative Example 1

The raw material ratio of Comparative example 1 differs from that of Example 1 only in that the concentration of the proteinase K in the first component was 2 U/mL, and other component ratios remained unchanged. The test method is the same as Example 1.

Figure 10:
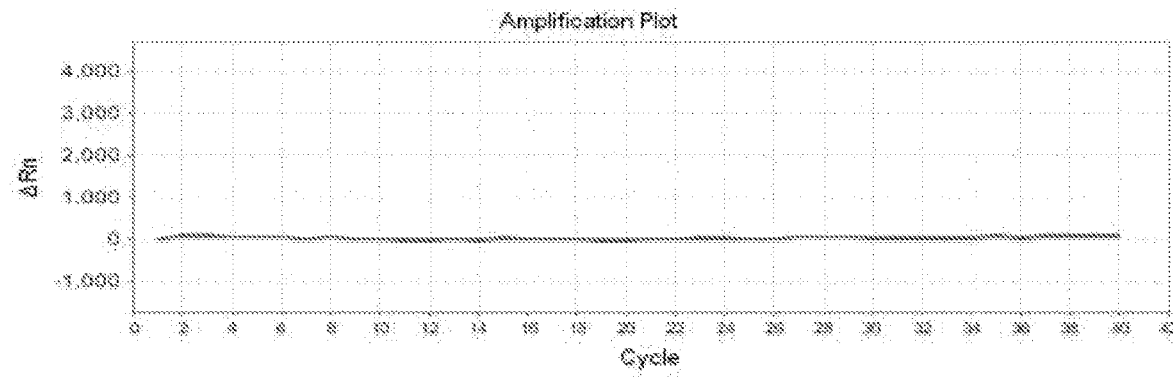
FIG. 10 is a schematic diagram of test results of Comparative Example 1 of the present disclosure.

The results of the amplification are illustrated in FIG. 10.

Conclusion: it can be seen from FIG. 10 that, when the concentration of the proteinase K is too low, it will affect the effect of the first component on the sample pyrolysis, thereby affecting the PCR amplification results. It indicates that the concentration of the proteinase K in the first component is very important.

Comparative Example 2

The raw material ratio of Comparative example 2 differs from that of Example 1 only in that both the concentration of EDTA and the concentration of EGTA in the first component were 0 mM, and other component ratios remained unchanged. The test method is the same as Example 1.

Figure 11:
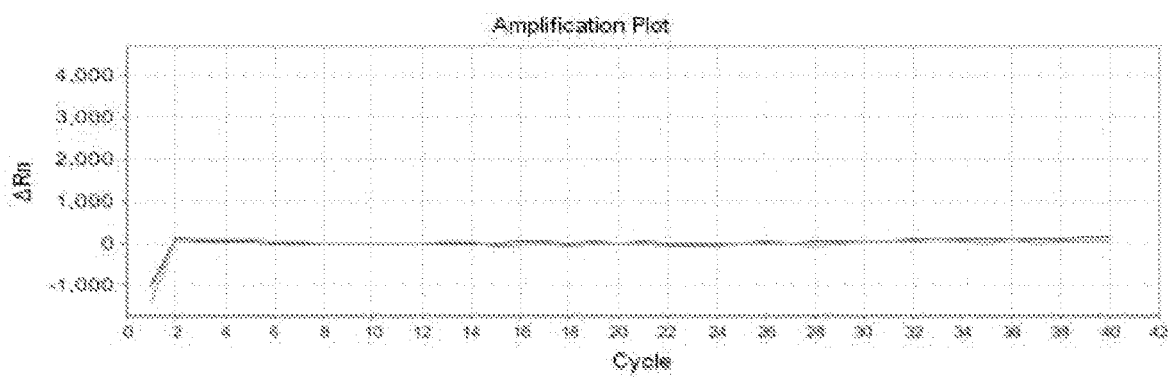
FIG. 11 is a schematic diagram of test results of Comparative Example 2 of the present disclosure.

The results of the amplification are illustrated in FIG. 11.

Conclusion: it can be seen from FIG. 11 that, when the ingredients of EDTA and EGTA are removed, the effect of the first component on the sample pyrolysis will be affected, thereby affecting the PCR amplification results. It indicates that the EDTA and EGTA play an important role in the first component.

Comparative Example 3

The raw material ratio of Comparative example 3 differs from that of Example 1 only in that the concentration of the saponin in the first component was 10%, and other component ratios remained unchanged. The test method is the same as Example 1.

Figure 12:
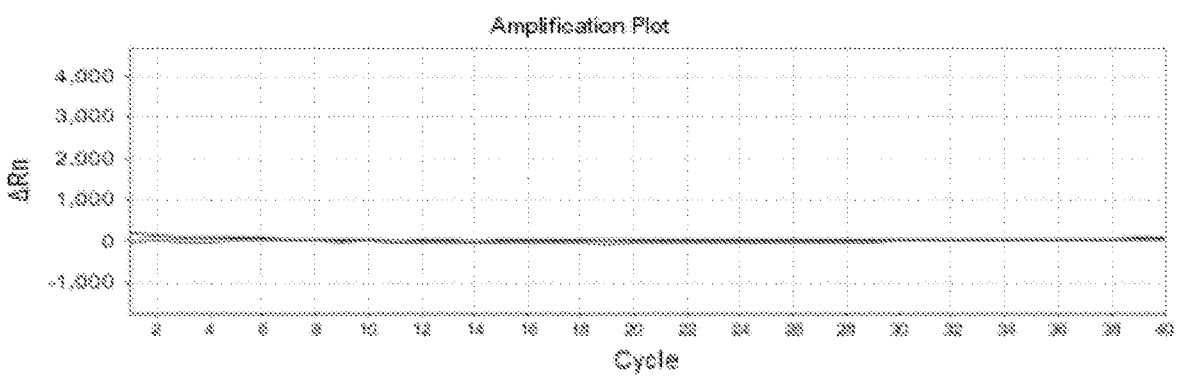
FIG. 12 is a schematic diagram of test results of Comparative Example 3 of the present disclosure.

The results of the amplification are illustrated in FIG. 12.

Conclusion: it can be seen from FIG. 12 that, when the concentration of the saponin is too high, it will affect the effect of the first component on the sample pyrolysis, thereby affecting the PCR amplification results. It indicates that the concentration of the saponin in the first component is very important.

Comparative Example 4

The raw material ratio of Comparative example 4 differs from that of Example 1 only in that the concentration of the magnesium chloride in the second component was 0.2 mM, and other component ratios remained unchanged. The test method is the same as Example 1.

Figure 13:
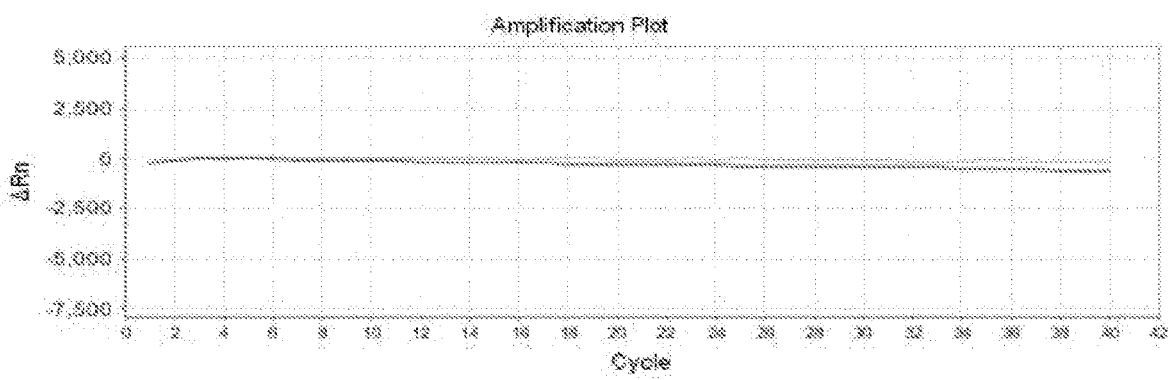
FIG. 13 is a schematic diagram of test results of Comparative Example 4 of the present disclosure.

The results of the amplification are illustrated in FIG. 13.

Conclusion: it can be seen from FIG. 13 that, when the concentration of the magnesium chloride is too low, the results of PCR reaction using the second component will be affected. It indicates that the concentration of the magnesium chloride in the second component is very important.

Comparative Example 5

The raw material ratio of Comparative example 5 differs from that of Example 1 only in that the concentration of the HEPES in the second component was 2 mM, and other component ratios remained unchanged. The test method is the same as Example 1.

Figure 14:
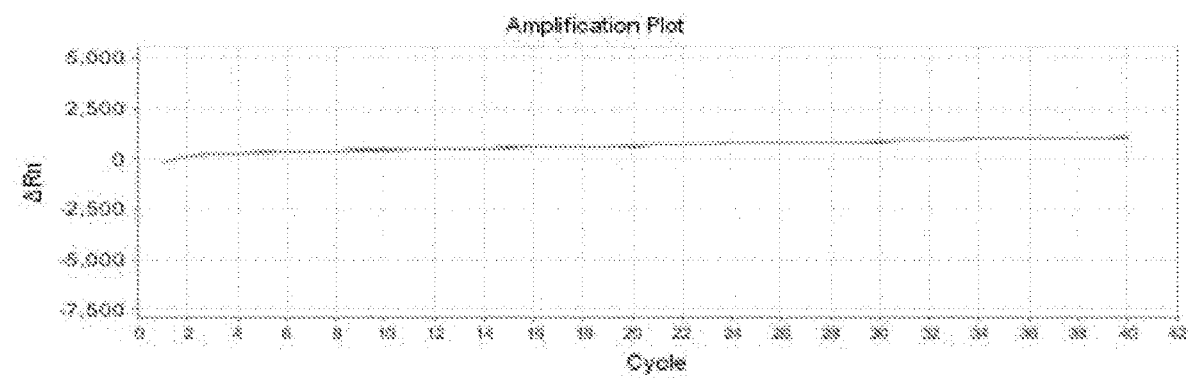
FIG. 14 is a schematic diagram of test results of Comparative Example 5 of the present disclosure.

The results of the amplification are illustrated in FIG. 14.

Conclusion: it can be seen from FIG. 14 that, when the concentration of the HEPES is too low, the results of PCR reaction using the second component will be affected. It indicates that the concentration of the HEPES in the second component is very important.

The composition and diluent of the above-mentioned PCR reaction are described in detail below. It should be noted that, unless otherwise specified, the meanings of respective ingredients and concentrations in the present disclosure can be understood according to conventional interpretations in the field, such as Tris-HCl and Tween 20. In addition, Amplification Plot represents an amplification curve, and Cycle represents the number of cycles.

I. Preparation of Diluent

Certain amounts of target ingredients were weighed or aspirated to prepare a predetermined volume of diluent. In the diluent, magnesium chloride was 0.5 mmol/L to 15 mmol/L, sodium chloride was 1 mmol/L to 150 mmol/L, surfactant was 0.1% to 7%, glycerol was 2% to 20%, and water was added to the predetermined volume, and the aspirated Tris-HCl solution has a concentration of 1 mM to 100 mM and pH of 7.5 to 8.0. The surfactant was Tween 20, Tween 80, polyethylene glycol octylphenol ether, sodium dodecyl sulfate (SDS), sodium dodecyl benzenesulfonate, sodium dioctyl sulfosuccinate, or sodium glycocholate.

II. Property Test

10 μL of the pyrolyzed sample solution was added to 90 μL of a dilution buffer (the above-mentioned diluent) for dilution, and 5 μL of the diluted solution was added to the PCR reaction system to perform the amplification reaction, and the Ct value was read.

Example 4

1. Formula Composition of the Diluent

5% Glycerol, 2 mM magnesium chloride, 5 mM sodium chloride, 5 mM Tris-HCl, and 0.5% Tween 20. The pH of the added Tris-HCl was 7.6.

Composition of PCR Reaction System

Taq enzyme 1 U/reaction, dNTP 4 mM/reaction, 18s rRNA Assay (Thermo Fisher) 1 μL/reaction, and template 5 μL/reaction.

2. Property Test Results

The property test was performed according to the above method and the Ct value was read.

Figure 15:
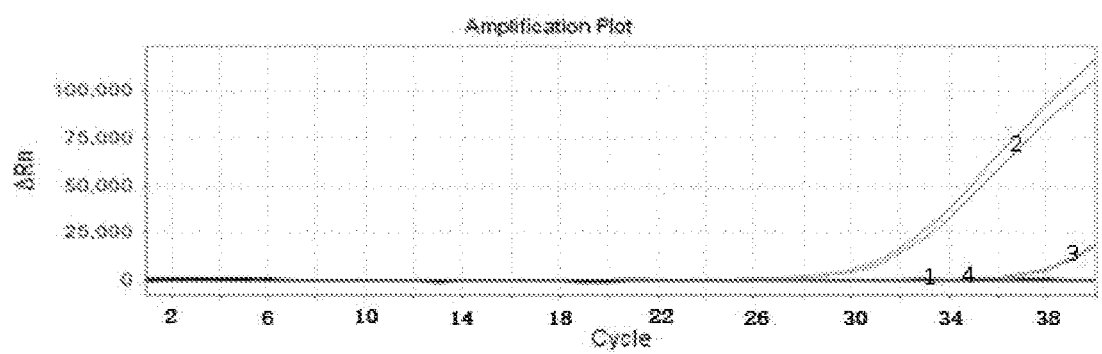
FIG. 15 is a schematic diagram of property test results of Example 4 of the present disclosure.

The test result is illustrated in FIG. 15, in which

Curve 1 represents a result of the amplification by directly adding the solution obtained after the sample was subjected to the pyrolysis process (pyrolysis stock solution) to the subsequent PCR reaction system;

Curve 2 represents a result of the amplification where the pyrolysis stock solution diluted with the dilution buffer (diluent) was added to the same PCR reaction system;

Curve 3 represents a result of the amplification where the pyrolysis stock solution diluted with H2O by the same multiple was added to the same PCR reaction system; and Curve 4 represents the amplification result of a negative control, in which the dilution buffer (diluent), as a template, was added to the same PCR reaction system.

Conclusion

Curve 1 is a result of the amplification where the solution obtained after the sample was subjected to the pyrolysis process was added to the subsequent PCR reaction system, exhibiting no amplification curve. Curve 2 is the case that the pyrolysis stock solution diluted with the dilution buffer was added to the same PCR reaction system, exhibiting a positive amplification curve. Curve 3 is the case that the pyrolysis stock solution was diluted with H2O by the same multiple, indicating that the sample is amplified, but the Ct value is significantly higher than that of the diluted sample diluted with the dilution buffer (the diluent of the present disclosure), and thus the buffering effect of the dilution buffer is better than that of H2O. Curve 4 is the negative control where the dilution buffer (diluent) serving as a template was added to the same PCR reaction system, exhibiting no amplification curve of the negative control, indicating that the dilution buffer can effectively buffer the pyrolysis solution and the PCR reaction system.

Example 5

1. Formula Composition of the Diluent

8% Glycerol, 6 mM magnesium chloride, 50 mM sodium chloride, 40 mM Tris-HCl, and 3% Tween 20. The pH of the added Tris-HCl was 8.0.

Composition of PCR Reaction System

Taq enzyme 1 U/reaction, dNTP 4 mM/reaction, 18s rRNA Assay (Thermo Fisher) 1 μL/reaction, and template 5 μL/reaction.

2. Property Test Results

The property test was performed according to the above method and the Ct value was read.

Figure 16:
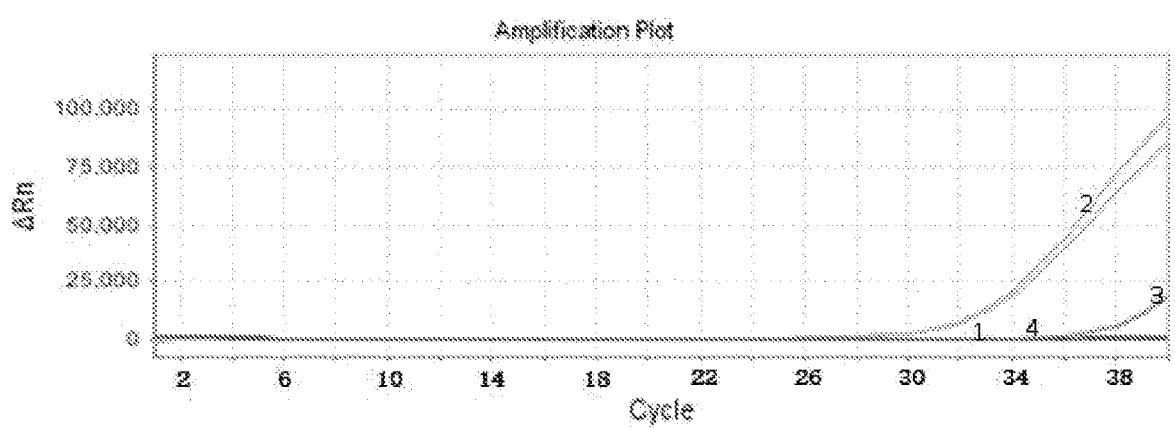
FIG. 16 is a schematic diagram of property test results of Example 5 of the present disclosure.

The test result is illustrated in FIG. 16, in which

Curve 1 represents a result of the amplification where the solution obtained after the sample was subjected to the pyrolysis process (pyrolysis stock solution) was directly added to the subsequent PCR reaction system;

Curve 2 represents a result of the amplification where the pyrolysis stock solution diluted with the dilution buffer (diluent) was added to the same PCR reaction system;

Curve 3 represents a result of the amplification where the pyrolysis stock solution diluted with H2O by the same multiple was added to the same PCR reaction system; and Curve 4 represents the amplification result of a negative control, in which the dilution buffer (diluent), as a template, was added to the same PCR reaction system.

Conclusion:

Curve 1 is a result of the amplification where the solution obtained after the sample was subjected to the pyrolysis process was added to the subsequent PCR reaction system, exhibiting no amplification curve. Curve 2 is the case that the pyrolysis stock solution diluted with the dilution buffer was added to the same PCR reaction system, exhibiting a positive amplification curve. Curve 3 is the case that the pyrolysis stock solution diluted with H2O by the same multiple, indicating that the sample is amplified, but the Ct value is significantly higher than that of the diluted sample diluted with the dilution buffer (the diluent of the present disclosure), and thus the buffering effect of the dilution buffer is better than that of H2O. Curve 4 is the negative control where the dilution buffer (diluent) serving as a template was added to the same PCR reaction system, exhibiting no amplification curve of the negative control, indicating that the dilution buffer can effectively buffer the pyrolysis solution and the PCR reaction system.

Example 6

1. Formula Composition of the Diluent

8% Glycerol, 6 mM magnesium chloride, 50 mM sodium chloride, 40 mM Tris-HCl, and 1% sodium dodecyl sulfate. The pH of the added Tris-HCl was 8.0.

Composition of PCR Reaction System

Taq enzyme 1 U/reaction, dNTP 4 mM/reaction, 18s rRNA Assay (Thermo Fisher) 1 μL/reaction, and template 5 μL/reaction.

2. Property Test Results

The property test was performed according to the above method and the Ct value was read.

Figure 17:
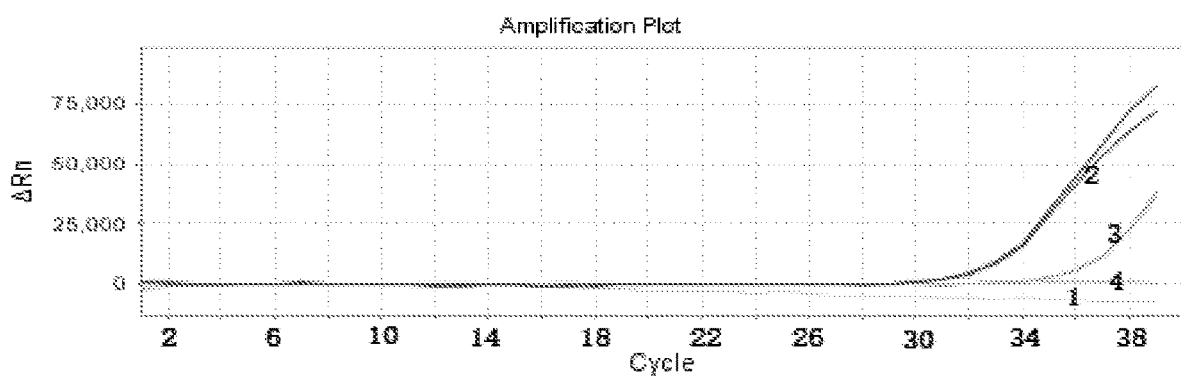
FIG. 17 is a schematic diagram of property test results of Example 6 of the present disclosure.

The test result is illustrated in FIG. 17, in which

Curve 1 represents a result of the amplification where the solution obtained after the sample was subjected to the pyrolysis process (pyrolysis stock solution) was directly added to the subsequent PCR reaction system;

Curve 2 represents a result of the amplification where the pyrolysis stock solution diluted with the dilution buffer (diluent) was added to the same PCR reaction system;

Curve 3 represents a result of the amplification where the pyrolysis stock solution diluted with H2O by the same multiple was added to the same PCR reaction system; and Curve 4 represents the amplification result of a negative control, in which the dilution buffer (diluent), as a template, was added to the same PCR reaction system.

Conclusion

Curve 1 is the result of the amplification where the solution obtained after the sample was subjected to the pyrolysis process was added to the subsequent PCR reaction system, exhibiting no amplification curve. Curve 2 is the case that the pyrolysis stock solution diluted with the dilution buffer was added to the same PCR reaction system, exhibiting a positive amplification curve. Curve 3 is the case that the pyrolysis stock solution diluted with H2O by the same multiple, indicating that the sample is amplified, but the Ct value is significantly higher than that of the diluted sample diluted with the dilution buffer (the diluent of the present disclosure), and thus the buffering effect of the dilution buffer is better than that of H2O. Curve 4 is the negative control that the dilution buffer (diluent) serving as a template was added to the same PCR reaction system, exhibiting no amplification curve of the negative control, indicating that the dilution buffer can effectively buffer the pyrolysis solution and the PCR reaction system.

Example 7

1. Formula Composition of the Diluent

5% Glycerol, 2 mM magnesium chloride, 5 mM sodium chloride, 5 mM Tris-HCl, and 0.1% polyethylene glycol octylphenol ether. The pH of the added Tris-HCl was 8.0.
Composition of PCR Reaction System Taq enzyme 1 U/reaction, dNTP 4 mM/reaction, 18s rRNA Assay (Thermo Fisher) 1 μL/reaction, and template 5 μL/reaction.

2. Property Test Results

The property test was performed according to the above method and the Ct value was read.

Figure 18:
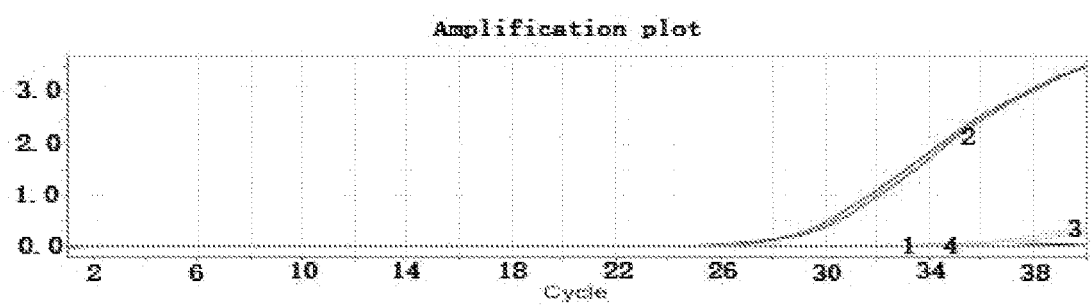
FIG. 18 is a schematic diagram of property test results of Example 7 of the present disclosure.

The test result is illustrated in FIG. 18, in which

Curve 1 represents a result of the amplification where the solution obtained after the sample was subjected to the pyrolysis process (pyrolysis stock solution) was directly added to the subsequent PCR reaction system;

Curve 2 represents a result of the amplification where the pyrolysis stock solution diluted with the dilution buffer (diluent) was added to the same PCR reaction system;

Curve 3 represents a result of the amplification where the pyrolysis stock solution diluted with H2O by the same multiple was added to the same PCR reaction system; and Curve 4 represents the amplification result of a negative control, in which the dilution buffer (diluent), as a template, was added to the same PCR reaction system.

Conclusion

Curve 1 is the result of the amplification where the solution obtained after the sample was subjected to the pyrolysis process was added to the subsequent PCR reaction system, exhibiting no amplification curve. Curve 2 is the case that the pyrolysis stock solution diluted with the dilution buffer was added to the same PCR reaction system, exhibiting a positive amplification curve. Curve 3 is the case that the pyrolysis stock solution diluted with H2O by the same multiple, indicating that the sample is amplified, but the Ct value is significantly higher than that of the diluted sample diluted with the dilution buffer (the diluent of the present disclosure), and thus the buffering effect of the dilution buffer is better than that of H2O. Curve 4 is the negative control where the dilution buffer serving as a template was added to the same PCR reaction system, exhibiting no amplification curve of the negative control, indicating that the dilution buffer can effectively buffer the pyrolysis solution and the PCR reaction system.

Comparative Example 6

The raw material ratio of Comparative example 6 differs from that of Example 1 only in that the concentration of Tween 20 was 8%, and other conditions were the same as those in Example 1.

Figure 19:
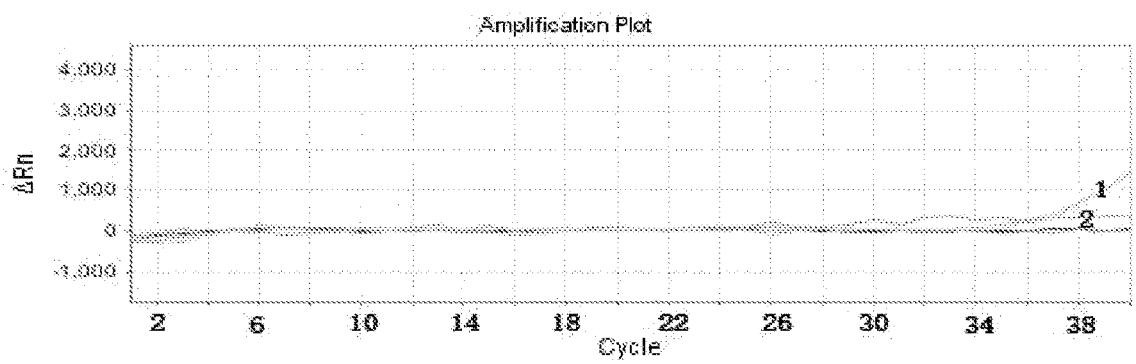
FIG. 19 is a schematic diagram of property test results of Comparative Example 6 of the present disclosure.

The test results are illustrated in FIG. 19.

Analysis and Conclusion

After the formula was changed, it was found that the sample diluted with the dilution buffer cannot be amplified to obtain a positive result (Curve 2), but the sample diluted with water can still be amplified to obtain a positive result (Curve 1), indicating that the sample is valid, but the sample diluted with the diluent of this formula ratio cannot be amplified. It indicates that the ratio of Tween 20 has a significant impact on the technical effect of the diluent composition of the present disclosure.

Comparative Example 7

The raw material ratio of Comparative example 7 differs from that of Example 1 only in that the concentration of glycerol was 30%, and other conditions are the same as those in Example 1.

Figure 20:
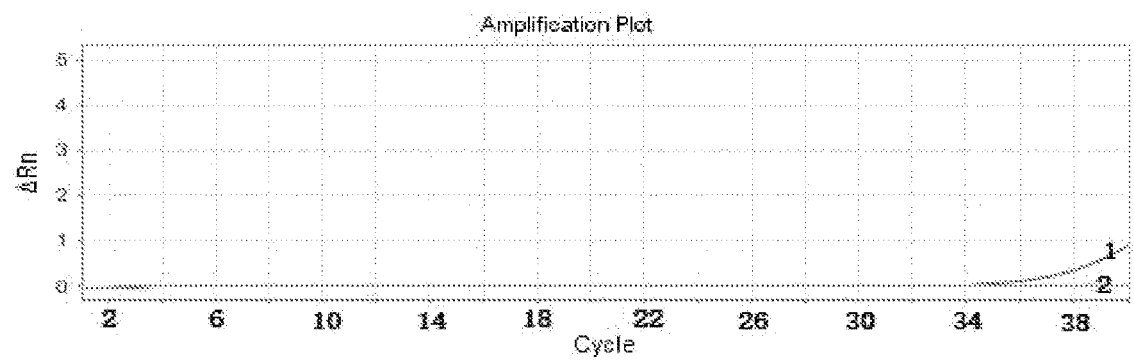
FIG. 20 is a schematic diagram of property test results of Comparative Example 7 of the present disclosure.

The test results are illustrated in FIG. 20.

Analysis and Conclusion

After the formula was changed, it was found that the sample diluted with the dilution buffer cannot be amplified to obtain a positive result (Curve 2), but the sample diluted with water can still be amplified to obtain a positive result (Curve 1), indicating that the sample is valid, but the sample diluted with the diluent of this formula ratio cannot be amplified. It indicates that the ratio of glycerol has a significant impact on the technical effect of the diluent composition of the present disclosure.

In addition, the terms "first" and "second" are only used for descriptive purposes, and cannot be understood as indicating or implying relative importance or implicitly indicating the number of indicated technical features. Therefore, the features defined with "first" and "second" may explicitly or implicitly include at least one of the features. In the description of the present disclosure, "plurality of" means at least two, such as two, three, etc., unless otherwise specifically defined.

In the present disclosure, unless otherwise clearly specified and limited, the terms such as "installed", "connection", "connected", and "fixed" should be understood in a broad sense, for example, indicating a fixed connection or a detachable connection, or integral connection; a mechanical connection, an electric connection, or a mutual communication; a direct connection, or an indirect connection through an intermediate medium, an internal connection of two components or the interaction relationship between two components, unless otherwise clearly defined. For those skilled in the art, the specific meanings of the above terms in the present disclosure can be understood according to specific circumstances.

In the specification, descriptions with reference to the terms "an embodiment", "some embodiments", "examples", "specific examples", or "some examples", etc., mean specific features, structures, materials or characteristics described in conjunction with the embodiment or example are included in at least one embodiment or example of the present disclosure. In this specification, the above terms are illustrative, and do not necessarily refer to the same embodiment or example. Moreover, the described specific features, structures, materials or characteristics can be combined in a suitable manner in any one or more embodiments or examples. In addition, those skilled in the art can combine the different embodiments or examples and the features of the different embodiments or examples described in this specification without contradicting each other.

Although the embodiments of the present disclosure are illustrated and described above, it can be understood that the above-mentioned embodiments are illustrative and should not be construed as limitations of the present disclosure. Those skilled in the art can make changes, modifications, substitutions, and variations based on the above-mentioned embodiments within the scope of the present disclosure.

What is claimed is:

1. A method for performing a PCR reaction using a PCR reaction system, the PCR reaction system comprising:
    a sample containing unit having a pyrolysis freeze-dried powder and a sample provided therein, the sample containing unit comprising a first liquid outlet/inlet;
    a diluent containing unit having a diluent provided therein, the diluent containing unit comprising a diluent outlet;
    a PCR reaction unit having a freeze-dried powder of a reverse transcriptase and PCR raw materials provided, the PCR reaction unit comprising a PCR reaction solution outlet and a pyrolyzed sample mixture inlet; and
    a piston unit comprising an injection chamber and a piston, the injection chamber comprising a second liquid outlet/inlet,
    wherein the second liquid outlet/inlet is connected to the first liquid outlet/inlet through a first pipeline, the second liquid outlet/inlet is connected to the diluent outlet through a second pipeline, the second liquid outlet/inlet is connected to the pyrolyzed sample mixture inlet through a third pipeline, and the PCR reaction solution outlet is connected to the diluent outlet through a fourth pipeline,
    the method comprising:
    subjecting the piston to a first movement processing, to allow a part of the diluent to enter the injection chamber, wherein the diluent is provided in the diluent containing unit;
    subjecting the piston to a second movement processing, to subject the part of the diluent entering the injection chamber, the pyrolysis freeze-dried powder, and the sample to a first mixing processing, wherein the pyrolysis freeze-dried powder and the sample are provided in the sample containing unit, and the first mixing processing is performed in the sample containing unit;
    subjecting a product of the first mixing processing to a pyrolysis processing, wherein the pyrolysis processing is performed in the sample containing unit;
    subjecting the piston to a third movement processing, to allow a product of the pyrolysis processing to enter the injection chamber;
    subjecting the piston to a fourth movement processing, to subject the product of the pyrolysis processing entering the injection chamber and the remaining part of the diluent to a second mixing processing, wherein the second mixing processing is performed in the diluent containing unit;
    subjecting the piston to a fifth movement processing, to allow a product of the second mixing processing to enter the injection chamber;
    subjecting the piston to a sixth movement processing, to subject the product of the second mixing processing entering the injection chamber and the freeze-dried powder of the reverse transcriptase and the PCR raw materials to a third mixing processing, wherein the freeze-dried powder of the reverse transcriptase and the PCR raw materials is provided in the PCR reaction unit, and the third mixing processing is performed in the PCR reaction unit; and
    subjecting a product of the third mixing processing to a PCR temperature cycle amplification processing, wherein the PCR temperature cycle amplification processing is performed in the PCR reaction unit.

2. The method according to claim 1, wherein the PCR temperature cycle amplification processing comprises:
    subjecting the product of the third mixing processing to a constant temperature processing; and
    subjecting a product of the constant temperature processing to a temperature cycle processing.

3. The method according to claim 2, wherein the PCR reaction system further comprises:
    a sample control valve provided on the first pipeline and configured to control a connection state between the first liquid outlet/inlet and the second liquid outlet/inlet;
    a dilution control valve provided on the second pipeline and configured to control a connection state between the diluent outlet and the second liquid outlet/inlet;
    a first PCR control valve provided on the third pipeline and configured to control a connection state between the pyrolyzed sample mixture inlet and the second liquid outlet/inlet; and
    a second PCR control valve provided on the fourth pipeline and configured to control a connection state between the diluent outlet and the PCR reaction solution outlet, and
    wherein the method further comprises:
    prior to the first movement processing, closing the sample control valve, the first PCR control valve, and the second PCR control valve, and opening the dilution control valve;
    subsequent to the first movement processing and prior to the second movement processing, closing the dilution control valve and opening the sample control valve;
    subsequent to the third movement processing and prior to the fourth movement processing, closing the sample control valve and opening the dilution control valve;
    subsequent to the fifth movement processing and prior to the sixth movement processing, closing the dilution control valve, and opening the first PCR control valve and the second PCR control valve; and subsequent to the constant temperature processing and prior to the temperature cycle processing, closing the first PCR control valve and the second PCR control valve.

4. The method according to claim 3, wherein the PCR reaction system further comprises:

a buffering unit provided on the fourth pipeline and comprising a PCR reaction solution inlet and a vent, wherein the second PCR control valve is connected to the PCR reaction solution inlet, and the diluent outlet is connected to the vent.

5. The method according to claim 1, wherein the PCR reaction system further comprises:

a sample containing unit seal provided on a surface of the first liquid outlet/inlet and configured to be used in a first sealing processing of the sample containing unit; and a diluent containing unit seal provided on a surface of the diluent outlet and configured to be used in a second sealing processing of the diluent containing unit, and wherein the method further comprises:

a pre-piercing processing comprising: subjecting the sample containing unit seal to a first piercing processing in advance, and subjecting the diluent containing unit seal to a second piercing processing in advance.

6. The method according to claim 5, wherein the first piercing processing is performed by a piercing device for the sample containing unit seal, and the second piercing processing is performed by a piercing device for the diluent containing unit seal.

7. The method according to claim 5, wherein at least one of the diluent containing unit seal and the sample containing unit seal is a sealing film.

8. The method according to claim 7, wherein the sealing film is formed of at least one of a tin foil paper, a laminating film, or a kraft paper.

9. The method according to claim 7, wherein the sealing film has a thickness ranging from 0.01 mm to 0.2 mm.

10. The method according to claim 7, wherein the sealing film has a thickness ranging from 0.05 mm to 0.1 mm.

11. A PCR reaction system, comprising:

a sample containing unit having a freeze-dried powder of pyrolysis raw materials and a sample provided therein, the sample containing unit comprising a first liquid outlet/inlet;

a diluent containing unit having a diluent provided therein, the diluent containing unit comprising a diluent outlet;

a PCR reaction unit having a freeze-dried powder of a reverse transcriptase and PCR raw materials provided therein, the PCR reaction unit comprising a PCR reaction solution outlet and a pyrolyzed sample mixture inlet; and a piston unit comprising an injection chamber and a piston, the injection chamber comprising a second liquid outlet/inlet, wherein the second liquid outlet/inlet is connected to the first liquid outlet/inlet through a first pipeline, the second liquid outlet/inlet is connected to the diluent outlet through a second pipeline, the second liquid outlet/inlet is connected to the pyrolyzed sample mixture inlet through a third pipeline, and the PCR reaction solution outlet is connected to the diluent outlet through a fourth pipeline.

12. The system according to claim 11, further comprising:

a sample control valve provided on the first pipeline and configured to control a connection state between the first liquid outlet/inlet and the second liquid outlet/inlet;

a dilution control valve provided on the second pipeline and configured to control a connection state between the diluent outlet and the second liquid outlet/inlet;

a first PCR control valve provided on the third pipeline and configured to control a connection state between the pyrolyzed sample mixture inlet and the second liquid outlet/inlet; and a second PCR control valve provided on the fourth pipeline and configured to control a connection state between the diluent outlet and the PCR reaction solution outlet.

13. The system according to claim 12, further comprising:

a buffering unit provided on the fourth pipeline and comprising a PCR reaction solution inlet and a vent, wherein the second PCR control valve is connected to the PCR reaction solution inlet, and the diluent outlet is connected to the vent.

14. The system according to claim 11, further comprising:

a sample containing unit seal provided on a surface of the first liquid outlet/inlet and configured to be used in a first sealing processing of the sample containing unit; and a diluent containing unit seal provided on a surface of the diluent outlet and configured to be used in a second sealing processing of the diluent containing unit.

15. The system according to claim 14, further comprising:

a piercing device for the sample containing unit seal, wherein the piercing device for the sample containing unit seal is configured to be used in a first piercing processing of the sample containing unit seal; and a piercing device for the diluent containing unit seal, wherein the piercing device for the diluent containing unit seal is configured to be used in a second piercing processing of the diluent containing unit seal.

16. The system according to claim 14, wherein at least one of the diluent containing unit seal and the sample containing unit seal is a sealing film.

17. The system according to claim 16, wherein the sealing film is formed of at least one of a tin foil paper, a laminating film, or a kraft paper.

18. The system according to claim 16, wherein the sealing film has a thickness ranging from 0.01 mm to 0.2 mm.

19. The system according to claim 11, wherein the freeze-dried powder of the pyrolysis raw materials comprises a metal ion chelating agent, sodium dodecyl sulfate, saponin, proteinase K, polyethylene glycol 3350, Tris-HCl, and water; and the freeze-dried powder of the reverse transcriptase and the PCR raw materials comprises mannitol, sucrose, chloride salt, bovine serum albumin, dNTPs, polyoxyethylene lauryl ether, HEPES, DNA polymerase, reverse transcriptase, RNase inhibitor, and water.

20. The system according to claim 11, wherein the diluent comprises polyol, chloride salt, Tris-HCl, surfactant, and water.

* * * * *